(12) United States Patent
Kaufman et al.

(10) Patent No.: US 7,130,457 B2
(45) Date of Patent: Oct. 31, 2006

(54) SYSTEMS AND GRAPHICAL USER INTERFACE FOR ANALYZING BODY IMAGES

(75) Inventors: Leon Kaufman, San Francisco, CA (US); Mikhail Mineyev, San Francisco, CA (US); Shelley Powers, Walnut Creek, CA (US); David Goldhaber, San Mateo, CA (US)

(73) Assignee: Accuimage Diagnostics Corp., South San Francisco, CA (US)

( * ) Notice: Subject to any disclaimer, the term of this patent is extended or adjusted under 35 U.S.C. 154(b) by 695 days.

(21) Appl. No.: 09/908,508

(22) Filed: Jul. 17, 2001

(65) Prior Publication Data

US 2003/0016850 A1    Jan. 23, 2003

(51) Int. Cl.
*G06K 9/00* (2006.01)
(52) U.S. Cl. ..................... 382/128; 715/700
(58) Field of Classification Search ........ 382/128–134, 382/115–118; 345/427; 715/700–866
See application file for complete search history.

(56) References Cited

U.S. PATENT DOCUMENTS

| | | | |
|---|---|---|---|
| 4,551,800 A | 11/1985 | Riederer et al. | |
| 5,325,293 A | 6/1994 | Dorne | |
| 5,359,513 A * | 10/1994 | Kano et al. | 382/128 |
| 5,528,492 A | 6/1996 | Fukushima | |
| 5,549,117 A | 8/1996 | Tacklind et al. | |
| 5,570,404 A | 10/1996 | Liang et al. | |
| 5,581,460 A * | 12/1996 | Kotake et al. | 705/3 |
| 5,655,084 A | 8/1997 | Pinsky et al. | |
| 5,664,177 A | 9/1997 | Lowry | |
| 5,672,877 A * | 9/1997 | Liebig et al. | 250/363.04 |
| 5,704,371 A | 1/1998 | Shepard | |
| 5,713,358 A | 2/1998 | Mistretta et al. | |
| 5,729,620 A | 3/1998 | Wang | |
| 5,807,256 A | 9/1998 | Taguchi et al. | |
| 5,832,450 A | 11/1998 | Myers et al. | |
| 5,832,504 A | 11/1998 | Tripathi et al. | |
| 5,895,461 A | 4/1999 | De La Huerga et al. | |
| 5,911,133 A | 6/1999 | Soble | |
| 5,917,929 A | 6/1999 | Marshall et al. | |
| 5,950,207 A | 9/1999 | Mortimore et al. | |
| 5,954,650 A * | 9/1999 | Saito et al. | 600/425 |
| 5,971,767 A | 10/1999 | Kaufman et al. | |
| 5,982,953 A * | 11/1999 | Yanagita et al. | 382/294 |
| 5,986,662 A | 11/1999 | Argiro et al. | |
| 5,987,094 A | 11/1999 | Clarke et al. | |
| 5,987,345 A * | 11/1999 | Engelmann et al. | 600/407 |
| 6,014,452 A | 1/2000 | Zhang et al. | |

(Continued)

OTHER PUBLICATIONS

Jeffrey Solomon, Brigitte Widemann, Kathy Warren, Frank Balis, Nicholas Patronas; "Automatic Lesion Detection and Volume Measurement in MR Imaging of Plexiform Neurofibromas"; IEEE; 2002.*

(Continued)

*Primary Examiner*—Bhavesh M. Mehta
*Assistant Examiner*—Craig W. Kronenthal
(74) *Attorney, Agent, or Firm*—Townsend and Townsend and Crew LLP

(57) ABSTRACT

Systems and graphical user interfaces for analyzing body images. In an exemplary embodiment, the present invention provides a graphical user interface having a display coupled to a microprocessing device and a memory device. The graphical user interface has an electronic representation of a first body image and a second body image and an electronic map representing the position of nodules on the first body image and second body image.

41 Claims, 20 Drawing Sheets

U.S. PATENT DOCUMENTS

| | | | |
|---|---|---|---|
| 6,029,138 | A | 2/2000 | Khorasani et al. |
| 6,049,622 | A | 4/2000 | Robb et al. |
| 6,061,695 | A | 5/2000 | Slivka et al. |
| 6,075,879 | A | 6/2000 | Roehrig et al. |
| 6,083,162 | A | 7/2000 | Vining |
| 6,122,351 | A | 9/2000 | Schlueter, Jr. et al. |
| 6,133,918 | A | 10/2000 | Conrad et al. |
| 6,161,080 | A | 12/2000 | Aouni-Ateshian et al. |
| 6,182,029 | B1 | 1/2001 | Friedman |
| 6,190,334 | B1 | 2/2001 | Lasky et al. |
| 6,205,871 | B1 | 3/2001 | Soloner et al. |
| 6,206,829 | B1 | 3/2001 | Iliff |
| 6,215,893 | B1 * | 4/2001 | Leshem et al. ............. 382/128 |
| 6,226,352 | B1 | 5/2001 | Salb |
| 6,240,201 | B1 | 5/2001 | Xu et al. |
| 6,253,214 | B1 | 6/2001 | Hall et al. |
| 6,266,453 | B1 * | 7/2001 | Hibbard et al. ............. 382/294 |
| 6,304,848 | B1 | 10/2001 | Singer |
| 6,317,617 | B1 | 11/2001 | Gilhuijs et al. |
| 6,348,793 | B1 | 2/2002 | Balloni et al. |
| 6,363,163 | B1 * | 3/2002 | Xu et al. ..................... 382/130 |
| 6,549,646 | B1 | 4/2003 | Yeh et al. |
| 6,560,476 | B1 | 5/2003 | Pelletier et al. |
| 6,640,001 | B1 | 10/2003 | Roehrig et al. |
| 6,754,374 | B1 * | 6/2004 | Miller et al. ................ 382/128 |
| 6,795,521 | B1 | 9/2004 | Hsu et al. |
| 6,901,277 | B1 | 5/2005 | Kaufman et al. |
| 2002/0021829 | A1 * | 2/2002 | Doi et al. .................... 382/131 |
| 2002/0028008 | A1 * | 3/2002 | Fan et al. .................... 382/131 |
| 2003/0028401 | A1 | 2/2003 | Kaufman et al. |
| 2004/0094167 | A1 * | 5/2004 | Brady et al. ................ 128/916 |

OTHER PUBLICATIONS

Agatston et al., "Quantification of Coronary Artery Calcium Using Ultrafast Computed Tomography," *JAAC*, (Mar. 15, 1990) vol. 15, No. 4, pp. 827-832.

Brown et al., "Method for segmenting chest CT image data using an anatomical model: Preliminary results" *IEEE Transactions on Medical Imaging* (1997) 16(6):828-839.

Brown et al., "Knowledge-based segmentation of thoracic computed tomography images for assessment of split lung function" *Med. Phys.* (2000) 27(3):592-598.

Brown et al., "Patent-specific models for lung nodule detection and surveillance in CT images" *SPIE Medical Imaging* (2001) In Press, 9 pages total.

Brown et al., "Model-based segmentation architecture for lung nodule detection in CT" *Radiology* (2000) 217(P):207.

Pfefferbaum et al., "Computer-interactive method for quantifying cerebrospinal fluid and tissue brain CT scans: Effects of aging" *Journal of Computer Assisted Tomography* (1986) 10(4):571-578.

Rapid Display™ [Product Brochure] Deus Technologies, 1700 Research Blvd., Suite 104, Rockville, MD, 20850, USA, telephone: 301-762-4442, 2 pages total.

Zhao et al., "Two-dimensional multi-criterion segmentation of pulmonary nodules on helical CT images" *Med. Phys.* (1999) 26(6):889-895.

Zhu et al., "Accuracy of area measurements made from MRI images compared with computer tomography" *Journal of Computer Assisted Tomography* (1986) 10(1):96-102.

U.S. Appl. No. 11/139,157 as filed May 27, 2005 with copy of filing receipt.

U.S. Appl. No. 60/306,311 as filed Jul. 17, 2001 with copy of filing receipt.

OmniCAD™ Clinical Advances by Design brochure, "Improving Sensitivity and Efficiency in Lung CT Nodule Detection," R2Technology, Inc. Sunnyvale, CA.

Swensen et al., "Computed Tomographic Screening for Lung Cancer: Home Run of Foul Ball," *Mayo Clin Proc.*, 78:1187-1188 (2003).

Tao et al., "Characterization of Small Nodules by Automatic Segmentation of X-ray Computed Tomography Images," *J. Comput. Assist Tomogr.*, 28(3):372-377 (2004).

* cited by examiner

164 →

| Lung | Mediastinum | Lesions |
| Chest Wall | Heart and Aorta |

☐ Normal
☐ Mild calcification in coronary arteries
☐ Moderate calcification in coronary arteries
☐ Marked calcification in coronary arteries
☐ Small amount of pericardial fluid
☐ Moderate amount of pericardial fluid
☐ Marked amount of pericardial fluid
☐ Small hiatal hernia
☐ Moderate hiatal hernia
☐ Large hiatal hernia
☐ Other

166 →

Statistics

ROI: ___ pix    ___ mm2    ___ mm3

Value (HU)
Min: ___  Max: ___        Median: ___
Mean: ___ Std: ___        Total Sum: ___
Diameter 1: ___           Diameter 2: ___

| Add | Delete | Cancel |

View data
○ Composite    ○ By slab

SHOW: | Lesion | Tags | Text |

| Lung | Mediastinum | Lesions |

| Chest Wall | Heart and Aorta |

Heart
- ☐ Normal
- ☐ Enlarged
- ☐ Other

Long Axis _____
Short Axis _____

Aorta
- ☐ Normal caliber
- ☐ No calcification
- ☐ Moderate calcification
- ☐ Marked calcification
- ☐ Other Diameter _____

Statistics

ROI: ___ pix   ___ mm2   ___ mm3

Value (HU)
Min: ___   Max: ___   Median: ___
Mean: ___  Std: ___   Total Sum: ___
Diameter 1: _____     Diameter 2: _____

| Add | Delete | Cancel |

View data:
○ Composite    ● By slab

SHOW:  | Lesion | Tags | Text |

| Lung | Mediastinum | Lesions |

| Chest Wall | Heart and Aorta |

Chest wall
☐ Normal
☐
☐ Other

Spine
☐ Normal
☐ Mild anterior osteophytic spurring
☐ Moderate osteophytic spurring
☐ Severe osteophytic spurring
☐ Minimal osteoarthritic changes, age typical
☐ Moderate degenerative disc disease
☐ Severe degenerative disc disease
☐ Other

Statistics

ROI: ___ pix    ___ mm2    ___ mm3

Value (HU)
Min: ___   Max: ___        Median: ___
Mean: ___  Std: ___         Total Sum: ___
Diameter 1: ___             Diameter 2: ___

| Add | Delete | Cancel |

View data
○ Composite   ● By slab

SHOW:  | Lesion | Tags | Text |

| Lung | Mediastinum | Lesions |

| Chest Wall | Heart and Aorta |

Lesion # N

- ☐ Right Lower Lobe
- ☐ Left Lower Lobe
- ☐ Right middle
- ☐ Left middle
- ☐ Right upper
- ☐ Left upper
- ☐ Other

| N | Count | Area | Vol | Size | Mean | Std |

174

Total

178

Statistics

ROI: ___ pix   ___ mm2   ___ mm3

Value (HU)
Min: ___  Max: ___     Median: ___
Mean: ___  Std: ___     Total Sum: ___
Diameter 1: ___        Diameter 2: ___

176

| Add | Delete | Cancel |

View data
○ Composite   ○ By slab

SHOW:  | Lesion | Tags | Text |

Figure 16

Findings: /218

1. Lungs: (x) non-calcified nodule(s) (is/are) identified as follows
(x) segment of (y) lobe measuring # x # x # mm; n)..........
Not other focal or diffuse parenchymal lesion is identified.

2. MEDIASTINUM: No clinically significant mediastinal, hilar or other intrathoracic adenopathy is seen.

3. HEART and THORACIC AORTA: The thoracic aorta is of normal size and appearance. No aortic or valve calcifications are seen. The pericardial surface is clear.

4. CHEST WALL: No significant chest wall abnormality is seen. The bony structures of the spine are normal in appearance for age.

/220

Conclusion: A focal nodule is identified that requires follow up and further investigation. Review of any prior chest x-rays or CT chest studies is suggested, and a full CT chest with contrast to assess the nodule characteristics or a PET scan is suggested. Early detection of lung cancer is complex. The main purpose of the CT study is to identify a nodule at its smallest size, when it can be most effectively treated. You should discuss this report with your physician who can use the knowledge of your full clinical history and other diagnostic tests to assist you in assessing the significance of these findings.
•

*The (your name) scanning facility is intended as a Chest screening and lung cancer facility only and is not considered a substitute for a physician's examination. All recommendations from our center are based solely upon information supplied by the conventional risk factor questionnaire and by the EBT scan results. The patient's own physician is best able to make definitive therapeutic decisions.*

_____
Reading Physician's Signature

Figure 18D

SYSTEMS AND GRAPHICAL USER INTERFACE FOR ANALYZING BODY IMAGES

CROSS-REFERENCES TO RELATED APPLICATIONS

The present application is related to U.S. patent application Ser. No. 09/908,432, filed herewith and entitled "Customizable Lung Report Generator" and U.S. patent application Ser. No. 09/908,466, filed concurrently herewith and entitled "Methods and Systems for Generating a Lung Report," each of which is incorporated by reference.

BACKGROUND OF THE INVENTION

The present invention relates generally to systems, methods, software, and graphical user interfaces for displaying and analyzing body images and for generating organ reports. More particularly, the present invention relates to graphical user interfaces and systems for analyzing one or more thoracic CT datasets to track and analyze lung nodules and other lung parameters.

Lung cancer is one of the most common forms of cancer among both men and women. Advances in medical imaging, such as CT and MRI scanning, have made it possible to localize and track early stage nodules that were previously non-detectable. However, such scanning protocols on a CT or MRI scanner typically generate no less than 40 images during a thoracic exam, while multi-slice protocols may generate 300 or more axial images. In order to analyze the dataset for lung nodules, the radiologist must review all of the slice images to localize the lung nodules. If a nodule is found in one slice image, the radiologist must then attempt to locate the nodule in the adjacent slices.

Unfortunately, such large amounts of data for each patient increases the probability that the radiologist will miss a potential nodule in their analysis of the image dataset, i.e., a "false negative." Tumors may be too small to be reliably detected, or their appearance may be obscured by the surrounding tissues such as vessels. Missed tumors may be detected months or years later in a follow-up examination. During this interval the tumor may grow larger and, in the worst case, metastasize.

In their early stages of development, malignant lung tumors may not be detected even upon careful inspection of the image dataset. The early detection of lung cancer is of particular importance because the overall survival rate from the disease is very low. It is generally believed that early detection of cancer is beneficial, but in the case of lung cancer this is not established because of the recentness of the technique. This patent provides tools which will help to elucidate this question.

To improve detection of lung nodules manual and semi-automatic pixel-based methods for segmenting CT images have been developed. One such method is manually creating a region of interest (ROI) delineating a nodule. A semiautomatic method requires a single, operator-defined seed point in which a computer algorithm will select similar contiguous gray-scale pixels that surround the seed point as the potential nodule. In another case it may be an operator-placed region of interest (such as a rectangle or ellipse) around the nodule.

While the proposed imaging methods offer significant potential to locate early stage nodules, still further improvements are desirable. In particular, if a small nodule or nodules are located in a first imaging scan, the radiologist will usually recommend that the patient return for a second, follow-up imaging scan. When the patient returns for the follow-up scan, the radiologist must relocate the nodules in the image scan and analyze the parameters of the nodules. Conventional imaging systems and methods do not provide an efficient way to determine if the nodules have increased in size, stayed the same, or the like.

Therefore, what is needed are reliable systems and user interfaces which allow the radiologist to quickly and accurately localize and track any changes in nodules found in an imaging scan. Furthermore, what is needed is an improved method for visualization and characterization of small malignant lung tumors on thoracic image scan that would enable earlier detection of these tumors or nodules so as to enable earlier detection.

BRIEF SUMMARY OF THE INVENTION

The present invention provides graphical user interfaces and systems that allow an operator to localize and analyze lung nodules in a baseline and follow up lung CT or MRI scan.

The graphical user interfaces of the present invention can be displayed on a display that is coupled to a microprocessing device and a memory device. The graphical user interface can display an electronic representation of a first body image taken at $t_1$ along a first plane and a second body image taken at $t_2$ along the first plane. At least one of the electronic representations are stored in the memory device. The graphical user interface also can display an electronic representation of at least one composite image of the first body image and the second body image.

The systems and graphical user interfaces of the present invention can be used to localize lung nodules and to determine the lung nodules relative position in the patient's lung, dimensions of the lung nodule, and other morphological parameters of a baseline image scan taken at $t_1$. After the nodules are located in the baseline scan, through manual, semiautomatic, or automatic localization techniques, the nodule information derived from the images can be analyzed by the operator to determine if the potential nodule is a a benign or malignant nodule or merely a part of the patient's vasculature.

The nodule information can be stored and later transferred to a follow up image scan taken at $t_2$ to ease the localization of the previously localized nodules in the follow-up scans. The stored nodule information provides a method that allows the operator to quickly determine if the nodules localized in the baseline scan have increased in size, the amount of increase, and the like. Additionally, the present invention can also allow the operator to quickly locate nodules—either manually or automatically with an analysis algorithm—that were not located in the baseline scan.

Typically, the graphical user interfaces of the present invention can be used to analyze thoracic images to track potential lung nodules over a time period. An operator can use the composite image to track the potential nodules (if any) in the first body image and the second body image. The composite image can provide the user a visual indication of any change in surface area, pixel area, or volume of the potential lung nodule.

In exemplary embodiments, the graphical user interfaces of the present invention displays a first image along a body slice taken at $t_1$ and a follow-up image of the same body slice taken at $t_2$ on a user output device, such as a computer monitor. Typically, the first and second images are displayed adjacent to each other so as to allow the operator to visually assess changes in the nodules.

Typically, each of the nodules can be localized on the image with a map of markers to indicate its lesion number and its relative position in the patient's lung. By choosing the marker, the operator can view the statistics of the marked nodule which can include, but is not limited to, nodule number, anatomic position, roundness, volume, surface area, major and minor axes, CT density or MRI signal intensity, density and signal standard deviation, signal histogram, roundness criteria, and the like.

Optionally, to improve the visualization of the nodules, the nodules in the baseline and follow-up images are colored differently from the surrounding tissue. Typically, the nodules displayed in the first image are displayed a different color than the nodules in the second image. Thus, if the first image and second image are superimposed over each other, the operator can visually assess the change in size (if any) of the superimposed nodules. Generally, the change in size of the nodule will be displayed in a third, different color.

A third comparison or composite image can be displayed on the user input device to illustrate changes (if any) between the first and second images. In particular, the comparison image can be used to illustrate the change in size of the nodules and any development of new nodules. Additionally, in some methods, a comparison chart can be displayed which quantitatively illustrates any change in size, volume, etc., of the previously localized nodules.

In another aspect, the present invention provides a system for interpreting thoracic images. The system includes a storage device for storing a first image scan and a second image scan, a user interface for displaying information, and a processor. The processor is programmed to access the storage device to display on the user interface an image from the first image scan and an image from the second image scan. The processor is also programmed to compare a lesion from the image from the first image scan and the lesion on the second image scan. The processor is also programmed to display differences of the lesion in the first image scan and the second image scan.

Comparing the lesion and displaying the differences of the lesion can take a variety of forms. For example, in some embodiments, the processor can provide a panel or chart which quantitatively displays changes of various parameters of the lesion (e.g., volume, surface area, diameter, number of pixels, or the like). Alternatively, the displaying of differences can include displaying the lesion in different colors so as to visually indicate the change in lesions. In yet other embodiments, the displaying of the changes can be shown via a composite image. The composite image can show the nodules superimposed over each other to visually indicate the change in size of the lesions. In the embodiments where the lesions are shown in different colors, the change in size of the lesions will generally be shown in a third, different color.

It should be appreciated, however, that displaying the differences can include other convention methods of illustrating changes or it can include a combination of the above described methods.

The systems of the present invention can further include an imaging device for collecting the image datasets. The image datasets can be coupled to a database or the systems of the present invention for processing. Optionally, the systems of the present invention can further include a printer for printing a body report, such as a lung report.

In another aspect, the present invention provides a system for displaying body images on a user output device. The system includes means for displaying a first mage in a first image window and means for displaying a second image in a second image window. The system further includes means for displaying a third image in a third window. The third image either a sum or a subtraction of the first and second image.

Optionally, the system includes a panel for displaying image information of the first, second, and third image. For systems that are used to analyze lung images, the information can include information on the number of lung nodules, the area, volume, surface area, number of pixels, change in size, and HU information of the lung nodules.

In a further aspect, the present invention provides a computer system for displaying two body images for comparison. The method comprises displaying a first and second image. A marked map of lesions is displayed in the first and second image to display the relative position of the nodules. The marked map can be used to illustrate the growth of new lesions, or the like. Optionally, a third composite image can be displayed to illustrate a change in size of any of the lesions.

A further understanding of the nature and advantages of the invention will become apparent by reference to the remaining portions of the specification and drawings.

BRIEF DESCRIPTION OF THE DRAWINGS

FIG. 13 is one sample lesion panel interface of the graphical user interface of the present invention, FIGS. 14–16 illustrate exemplary panels for other organs that are displayed in a graphical user interface of the present invention;

FIGS. 18A to 18D are exemplary pages of a lung report that can be generated by the methods and software of the present invention.

DETAILED DESCRIPTION OF THE INVENTION

Figure 1:
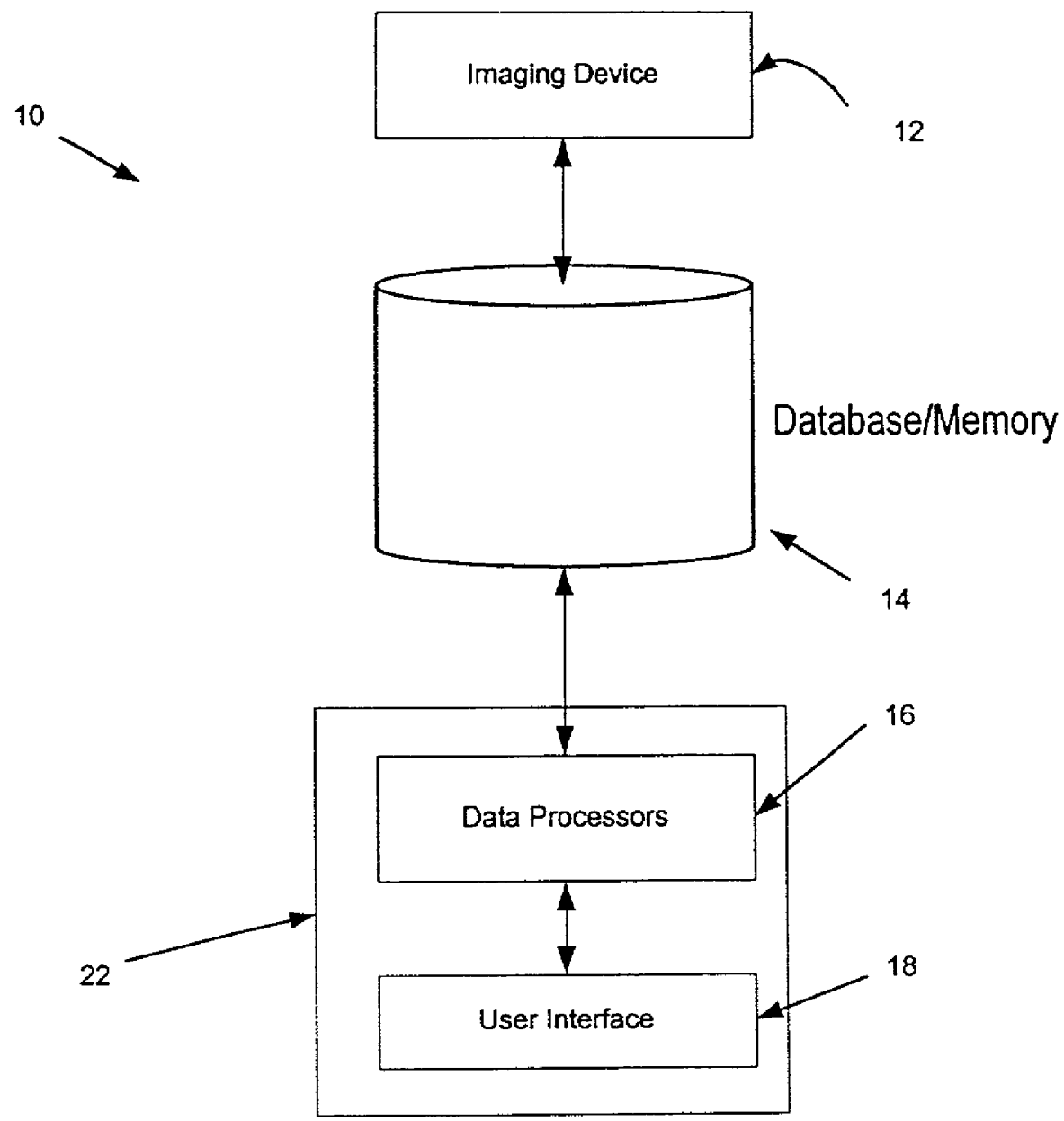
FIG. 1 schematically illustrates a simplified system of the present invention.

The present invention provides systems, software code, graphical user interfaces, and methods for displaying and analyzing lung CT or MRI image datasets of a patient. The lung datasets can be analyzed to map, track, and analyze the nodules in a series of lung slice images or image scans, as well as record other lung and chest abnormalities.

A lung slice image can be displayed on a user interface display for analysis by a radiologist or other operator. The methods of the present invention allows the radiologist to locate and map out the tumors, nodules, or lesions (hereinafter referred to as "nodules") that are both manually localized and/or automatically localized by the software of the present invention. The mapped nodules can be segmented and have its volume and other dimensions ascertained. Such nodule information can then be transferred onto a lung report, if desired.

Exemplary embodiments of the present invention may allow an operator to compare a first, baseline scan taken at $t_1$ with one or more follow-up dataset scans taken at $t_2$, $t_3$, etc. wherein $t_1$, $t_2$, and $t_3$ are various time points. If an operator locates one or more nodules in the baseline scan, the operator can use the methods and software of the present invention to relocate the previously located nodules and to compare the nodule parameters from the baseline scan with the nodule parameters from the follow up scan(s). The operator can compare changes in volume, changes in surface area, changes in other morphological parameters of the nodules, and the like. The present invention also can also be used to locate additional nodules that appear in the follow up scan that were not assessed (or present) in the baseline scan.

In order to compare the baseline image with the follow up image, the imaging technical parameters (e.g., slice thickness, beam collimation, kV, mAs, table incrementation, slice overlap, reconstruction parameters) of the baseline dataset scan and the follow-up dataset scan should substantially correspond.

If the imaging parameters of the two images are not consistent, it may be difficult to align the baseline and follow up images for comparison. Nevertheless, methodology exists for correcting for some differences. For instance, images can be rescaled to adjust for spatial resolution, slice thickness, slice overlap and rotation. While changes in imaging parameters such as kV in CT or timing parameters in MRI would impede comparison of tissue characteristics, they would not affect size and volume measurements. It should be appreciated however, that there will inherently be some differences in the baseline and follow-up images due to external factors such as the cardiac cycle or breathing pattern of the patient. Some of these may be ameliorated by retrospective or prospective gating techniques. A more complete disclosure of Retrospective Gating can be found in co-pending Provisional Patent Application Ser. No. 60/306, 311, entitled "Retrospective Gating," filed concurrently herewith, the complete disclosure of which is incorporated herein by reference. Thus, the images will typically not be exactly the same. Such deviations will generally not prevent a comparison of the baseline and follow up images as long as they are not so large as to affect the individual measurement itself in a significant manner.

If the imaging parameters are substantially the same, the images can be "aligned" to allow for comparison. Aligning can include manually aligning the baseline and follow up image, or automatically aligning the baseline and follow-up images using an aligning algorithm.

The present invention further provides a lung report generator for producing customizable body reports that can incorporate information derived from the operator's analysis of the image dataset(s). The lung report generator can analyze a single image scan or can compare a plurality of body scans and produce a customizable lung report. The lung report generator can use a customizable decision tree to analyze the information from the images and determine what information is displayed on the lung report. Typically, the decision tree will generate information related to the nodules, patient demographic information, medical history, a comparison to population data, radiologist recommendations, standards of practice of the community, or the like. The customization aspect allows different imaging sites or each physician to customize the lung report to meet their own needs. This customization reflects community standards, personal standing in areas where consensus is not universal, a different knowledge base, and intellectual biases.

The present invention also provides graphical user interfaces for display on a user interface output device, such as a computer monitor, for displaying and analyzing the body image dataset(s). The graphical user interfaces provides windows for showing one or more image planes and inputs that allow the operator localize and analyze lesions in the body image(s). For comparison studies, the graphical user interface further allows the operator to view and compare the images of a baseline scan with the images in the follow-up scan so as to track and analyze potential lung nodules. Such information will allow the operator to assess any changes (visually and/or quantitatively) in the nodules over the time period between the baseline scan and follow up scan.

The locations of the nodules on the graphical user interface can be indicated with a marker, such as a number, symbol, shape, color, or the like. The map of the lesions can then be automatically transferred to a follow up image dataset to indicate where the potential nodules are, or should be, located in the follow up image dataset. In other embodiments, the potential nodules can be automatically colored differently from the surrounding tissue to allow the operator to more easily visualize the nodules.

The graphical user interface generally allows the operator to display the baseline image side-by-side with a follow up image to allow the operator to visually assess the changes in the size or shape of the nodules. In exemplary configurations, the graphical user interface provides a third, comparison image that is a combination of the baseline and follow up images. The combination image can be a sum image, a subtraction image, or a superimposed image of the baseline images. In one configuration, the lesions in the baseline and follow up images can be displayed in different colors so as to provide improved visual assessment of the change in size and/or shape of the lesion. Thus, when the baseline and follow up images are superimposed over each other, the corresponding nodules having different colors provide a visual indication for the purpose of matching nodules, and also indicates to the operator changes in size of the nodule (if any) in the various image planes, even though, the results of quantitative measures are more robust for this latter purpose.

In many embodiments, a chart or panel can be displayed on the graphical user interface to quantitatively compare the nodules in the baseline and follow up images. The panel can provide numerical indications of the change in volume, roundness, surface area, HU, mean, standard deviation, density (e.g. HU in x-ray CT or signal intensity in MRI), and the like. The chart will generally indicate which nodule is attached to the numerical information through the use of the marker which is superimposed over the nodule(s).

While the remaining discussion will focus on analyzing lung images and generating a lung report, it should be appreciated that the present invention is not limited to analyzing lung images and producing lung reports. For example, the present invention can also be used to analyze other body organs such as for use in the colon, the vascular tree, brain, Calcium Scoring, the whole body, or the like.

Referring now to FIGS. 1–4, the systems 10 of the present invention can take a variety of forms. As illustrated in FIG. 1, the system 10 of the present invention includes an imaging device 12 (such as a helical or conventional CT scanner, MRI scanner, X-ray unit, nuclear imaging unit, positron emission tomography unit, ultrasound, or the like) that is in communication with a database or memory 14. An operator can use a computer station 22 that has data processor(s) 16 and user interface(s) 18 for accessing database 14 so as to process and view the image(s) and image data.

Figure 2:
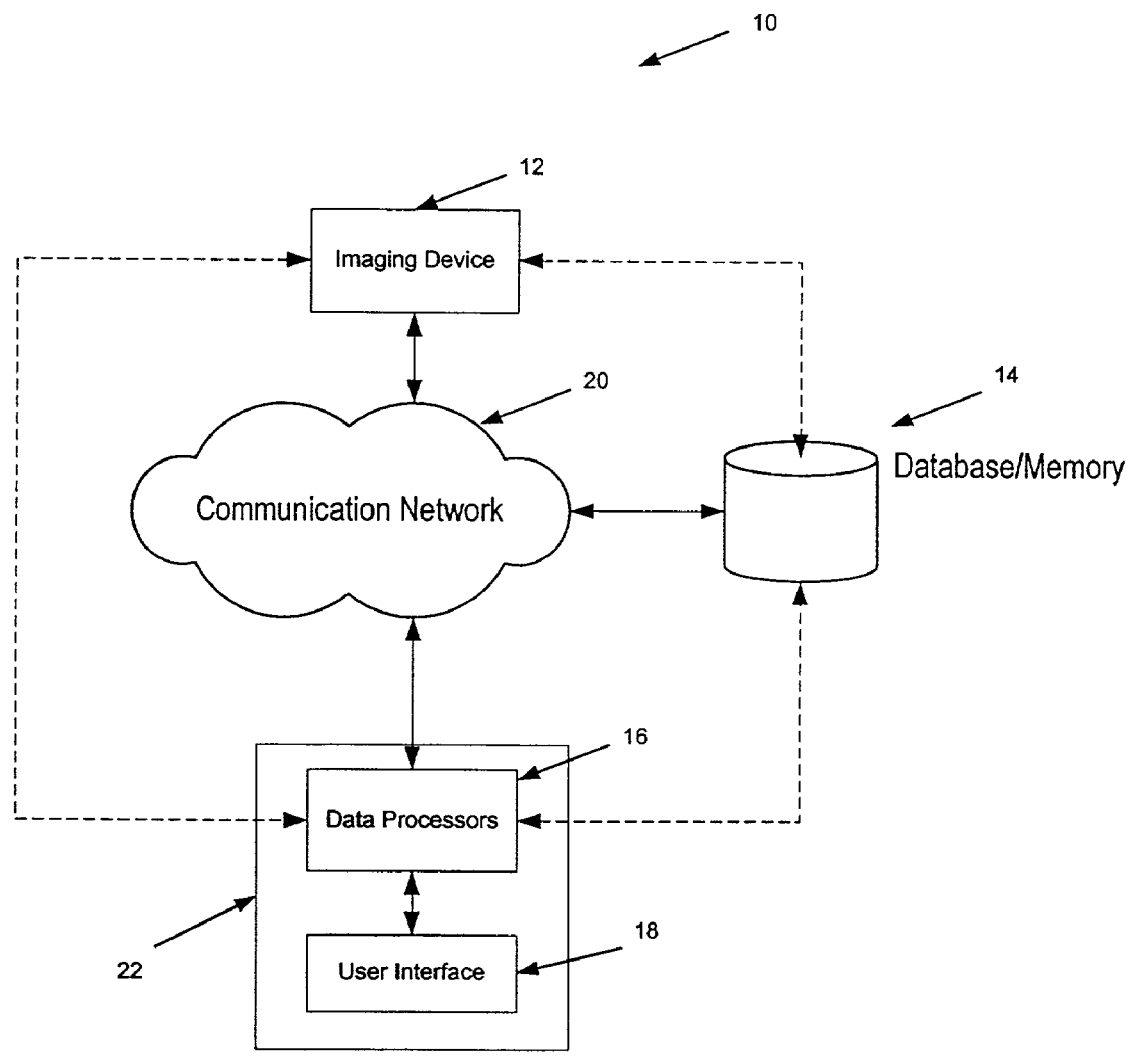
FIG. 2 schematically illustrates a simplified networked system of the present invention.

In a particular embodiment, as illustrated in FIG. 1, the system 10 of the present invention can be a stand-alone system and all of the components of the system can be located at the same imaging site. In other embodiments, as shown in FIG. 2, some or all of the components of the system can be distributed throughout a communication network 20. Some combination of the components of the system 10 can be located in a single imaging facility while other components of the system may be located remotely. For example, as shown with the dotted lines in FIG. 2, the imaging device 12 can be directly coupled to (or integral with) the computer station 22. In such embodiments, the image data can be logged into a local memory in the computer station (not shown) and/or sent via the communication network 20 to the remote database 14. Alternatively, images from a remote imaging device 12 can be sent to the computer station 22 and/or the database 14 via the communication network 20 for analysis.

Communication network 20 may be comprised of many interconnected computer systems and communication links. Communication links may be hardwire links, optical links, satellite or other wireless communication links, wave propagation links, or any other mechanisms for communication of information. While in one embodiment, communication network 20 is the Internet, in other embodiments, communication network 20 may be any suitable computer network, such as an intranet, a local area network (LAN), a metropolitan area network (MAN), a wide area network (WAN), or the like.

Figure 3:
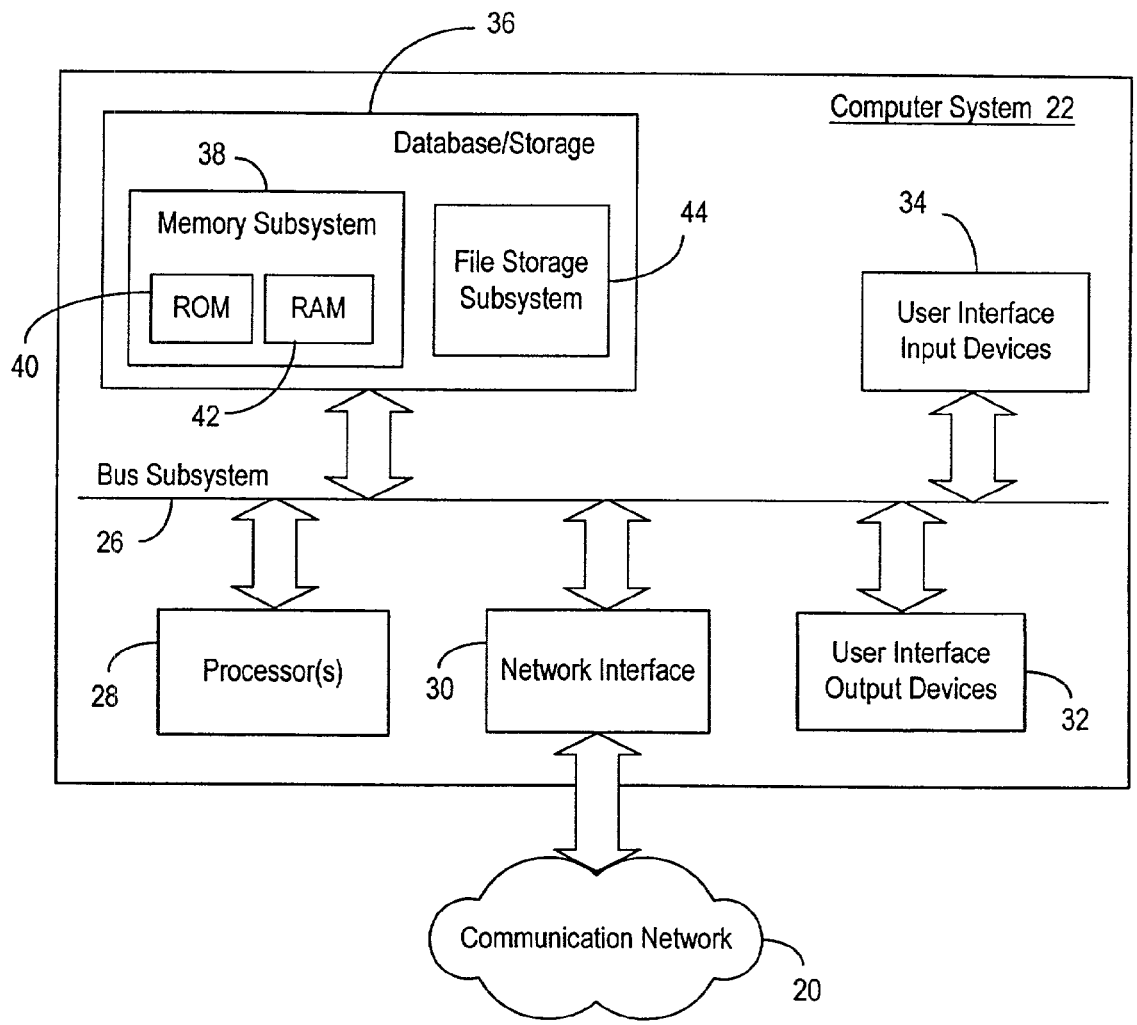
FIG. 3 schematically illustrates an exemplary computer station which incorporates the software code and methods of the present invention.

FIG. 3 is a simplified block diagram of an exemplary computer station 22 of the present invention. Computer station 22 typically includes at least one processor 28 which communicates with a number of peripheral devices via a bus subsystem 26. These peripheral devices may include a storage subsystem 36, comprising a memory subsystem 38 and a file storage subsystem 44, user interface input devices 34, user interface output devices 32, and a network interface subsystem 30. Network interface subsystem 30 provides an interface to outside networks, including an interface to communication network 20, and is coupled via communication network 20 to corresponding interface devices in other computer systems.

User interface input devices 34 may include a keyboard, pointing devices such as a mouse, trackball, touch pad, or graphics tablet, a scanner, foot pedals, a joystick, a touch-screen incorporated into the output device 32, audio input devices such as voice recognition systems, microphones, and other types of input devices. In general, use of the term "input device" is intended to include a variety of conventional and proprietary devices and ways to input information into computer system 24 or onto computer network 20.

User interface output devices 32 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of devices and ways to output information from computer system 24 to an operator or to another machine or computer system.

Storage subsystem 36 stores the basic programming and data constructs that provide the functionality of the various embodiments of the present invention. For example, database and modules implementing the functionality of the present invention may be stored in storage subsystem 36. These software modules are generally executed by processor 28. In a distributed environment, the software modules may be stored on a plurality of computer systems and executed by processors of the plurality of computer systems. Storage subsystem 36 typically comprises memory subsystem 38 and file storage subsystem 44.

Memory subsystem 38 typically includes a number of memories including a main random access memory (RAM) 42 for storage of instructions and data during program execution and a read only memory (ROM) 40 in which fixed instructions are stored. File storage subsystem 44 provides persistent (non-volatile) storage for program and data files, and may include a hard disk drive, a floppy disk drive along with associated removable media, a Compact Digital Read Only Memory (CD-ROM) drive, an optical drive, or removable media cartridges. One or more of the drives may be located at remote locations on other connected computers at other sites coupled to communication network 20. The databases and modules implementing the functionality of the present invention may also be stored by file storage subsystem 44.

Bus subsystem 26 provides a mechanism for letting the various components and subsystems of computer system 22 communicate with each other as intended. The various subsystems and components of computer system 22 need not be at the same physical location but may be distributed at various locations within distributed network 10. Although bus subsystem 26 is shown schematically as a single bus, alternate embodiments of the bus subsystem may utilize multiple busses.

Computer system 22 itself can be of varying types including a personal computer, a portable computer, a workstation, a computer terminal, a network computer, a module in the imaging unit, a mainframe, or any other data processing system. Due to the ever-changing nature of computers and networks, the description of computer system 22 depicted in FIG. 3 is intended only as a specific example for purposes of illustrating the preferred embodiment of the present invention. Many other configurations of computer system 22 are possible having more or less components than the computer system depicted in FIG. 3.

Figure 4:
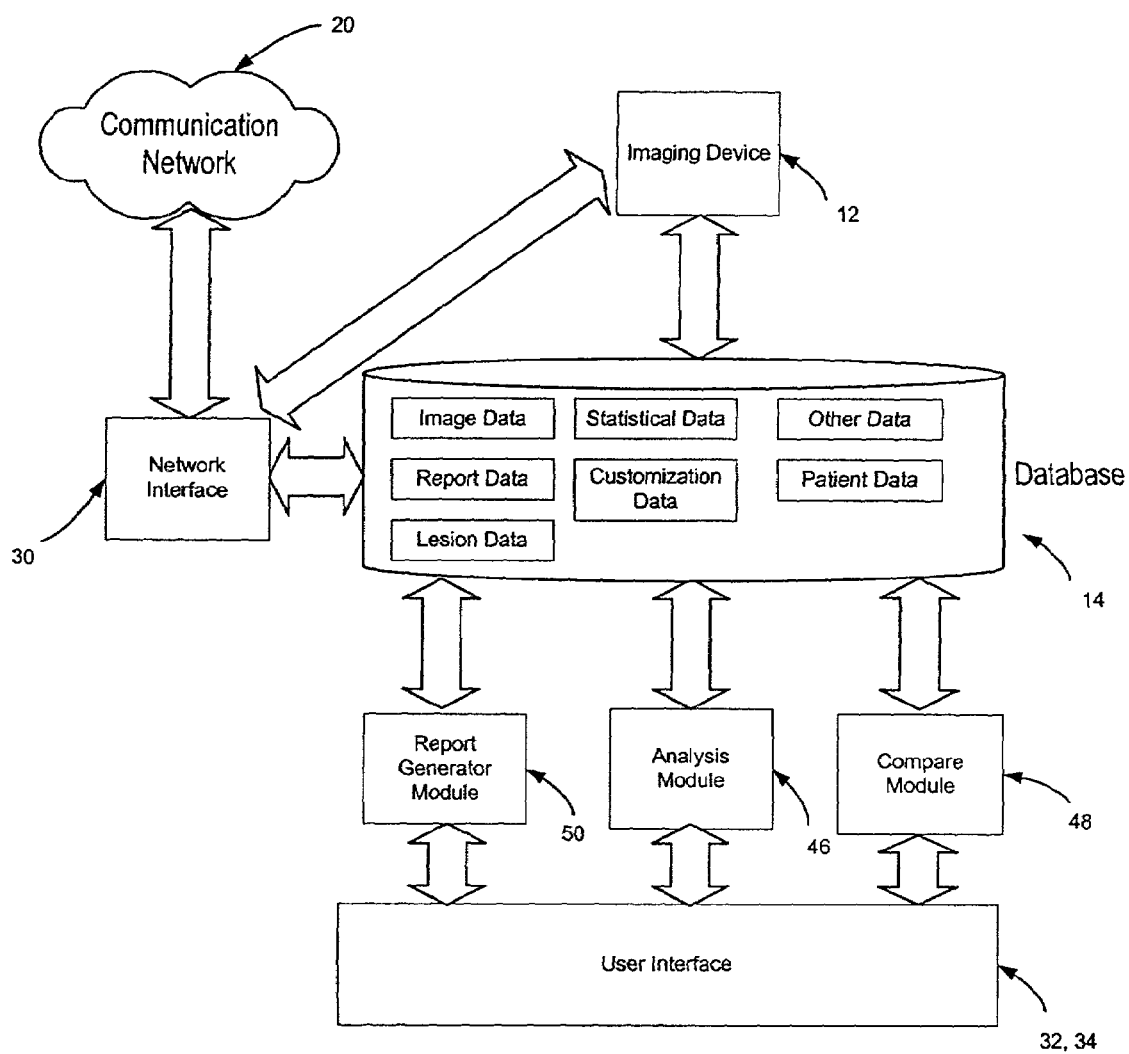
FIG. 4 schematically illustrates software modules communication with a database of the present invention.

FIG. 4 is a simplified block diagram depicting the various software modules executing on a computer system 22 of the present invention. Software of the present invention typically includes an analysis module 46 for analyzing and localizing nodules, comparison module 48 for comparing a baseline and follow up image dataset, and a report generator module 50 for generating a lung report.

Figure 5:
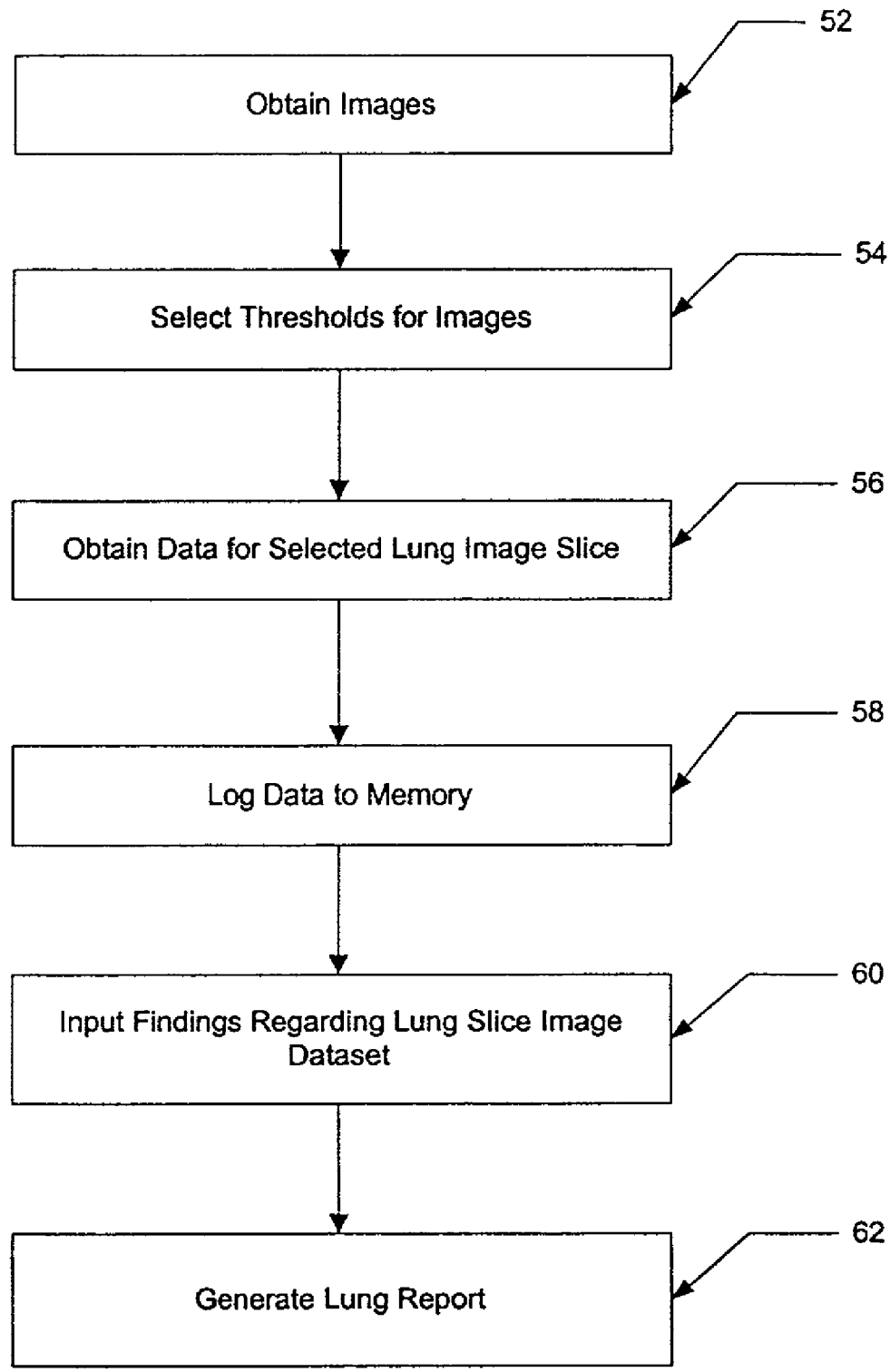
FIG. 5 illustrates a simplified method of generating a lung report the present invention.

As shown in FIG. 5, images of the target portion (e.g., lungs) of the patient can be acquired with an imaging device 12, such as a conventional or helical CT scanner, MRI scanner, or the like. (Step 52). It should be appreciated however, that various other types of images and imaging systems can be used to obtain the patient images, such as nuclear imaging, ultrasound, x-ray, digital x-ray, PET, and the like. The images of the target portion will typically be digitized and stored in a database 14 remote from the imaging device and/or within a local memory or database 36 in the computer system 22. The imaging parameters of the scan should also be logged into the database so as to allow for a comparison with a follow up scan that has similar imaging parameters.

Figure 9:
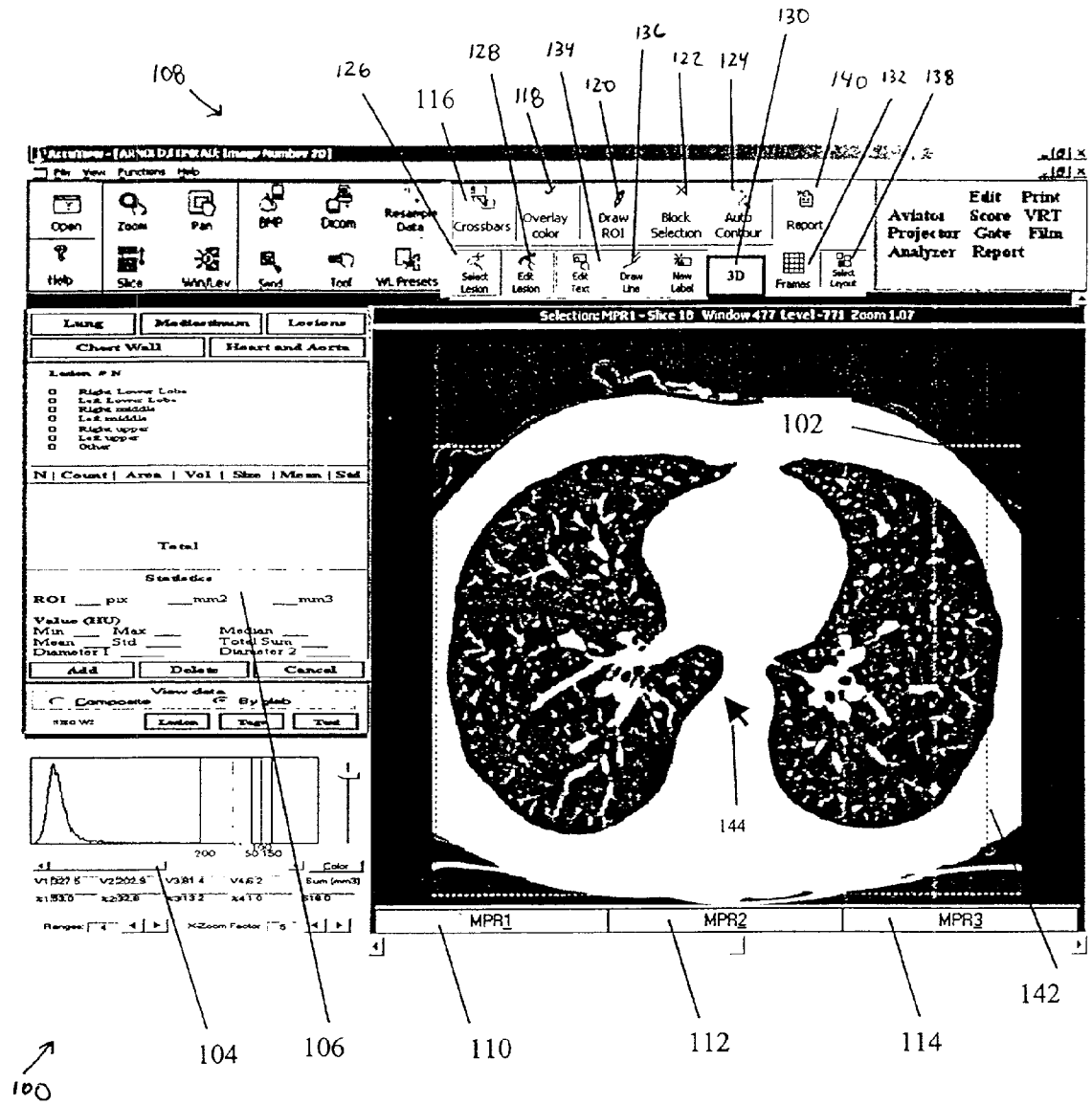
FIG. 9 illustrates an exemplary graphical user interface of the present invention.

When an operator desires to analyze the image data and/or produce a lung report, the operator will activate the software using conventional methods, such as clicking on an icon on the desktop with a cursor that is controlled by a mouse or other user input device 34 or voice recognition devices. The operator can request the patient image data via user interface 34 and the analysis module 46 can retrieve the requested information from database 14 and display the selected image(s) on user interface display 32. Generally, the image data will be displayed on a window 102 in graphical user interface 100. (FIG. 9). In some embodiments, the lung image will be shown as a single axial view. In other embodiments, three viewing planes (e.g., axial, sagittal, and coronal) of the image will be shown. In such embodiments, the coronal and sagittal view will have arbitrary locations, until the operator chooses, e.g., clicks on a point on one of the three views to set the point in which the image planes will correspond to. It should be appreciated, however, that it may be possible to display an oblique and/or reformatted image plane, if desired.

To improve the analysis of nodules in the lung image, the image data can then optionally be edited, either automatically by the analysis module 46 or manually by the operator, to set the thresholds of the image to separate vascular, interstitial, and emphasemic tissue from the image. (Step 54). Based on known tissue attenuation ranges, different tissue types (e.g., bone, tumors, etc.) can be identified by pixels within a specified gray level range. Setting the thresholds can be set by interactively moving corresponding bars on a histogram 104 to detect and filter out specific gray scale pixel intensity levels or using a Histogram Preset Button to remove the non-target tissue from the image(s). Typically, such Preset Buttons are configurable to allow the operator to customize the ranges of lung attenuation (HU) that is filtered out. It should be appreciated that gray level thresholding is merely one method of segmenting the lung image dataset and that other methods can be incorporated into the teachings of the present invention. For example, other methods of filtering out known tissue structures in the displayed image include the use of automated edge tracking algorithms, knowledge-based methods, and patient specific models, among others. Such methods are further described in Brown et al., "Method for Segmenting Chest CT Image Data Using an Anatomical Model: Preliminary Results," IEEE Transaction on Medical Imaging, Vol. 16, No. 6, December 1997, and Brown et al., "Patient-specific models for lung nodule detection and surveillance in CT images," SPIE Medical Imaging 2001, the complete disclosure of which is incorporated herein by reference.

Once the thresholding of the images is completed, the nodules in the image dataset can be selected for analysis. Such selection can be accomplished manually or automatically via a selection algorithm in the analysis module 46. One pixel-based method for selecting the lesion comprises manually tracing an outline of the potential nodule by manually tracing a region of interest (ROI) around each of the potential nodules by moving a mouse, joystick, or the like. Such tracing can require that the radiologist perform the same tracing function for each of the nodules in a series of the slice images. Such selection methods will eventually allow the computer software to log the anatomic position of the nodule, calculate the volume, surface area, and other morphological parameters of the potential nodule. In some semi-automated methods, the operator can select a potential nodule on one slice and analysis module 46 can automatically select the corresponding nodules either on the basis of spatial overlap or proximity or of gray-scaling in adjacent slice images. In other fully automated methods, the analysis module can use a selection algorithm to automatically select and map out the potential nodules in each of the slices. A further description of methods of selecting nodules can be found in Brown M. S. et al. "Knowledge-based segmentation of thoracic computed tomography images for assessment of split lung function," Med. Phys. 27 (3) pp. 592–598 March 2000, Brown, M. S. et al. "Model-Based Segmentation Architecture for Lung Nodule Detection in CT" Radiology 217(P):207, 2000 (Abstract), Zhao, B. et al. "Two-dimensional multi-criterion segmentation of pulmonary nodules on helical CT images," Med. Phys. 26 (6) pp. 889–895 June 1999, the complete disclosures of which are herein incorporated by reference. After the potential nodules have been selected, the operator can review the potential nodules selected. The operator will then have the option to accept or reject nodules that the operator does not believe is a nodule. Moreover, the operator further has the option to select other potential nodules that were not automatically chosen by analysis module 46.

Since nodules will often have the same signal intensity as blood vessels, chest wall or the like, problems in delineating the nodule may occur when the nodule or lesion is directly adjacent blood vessels, chest wall, or the like. In such cases analysis module 46 may have difficulty picking out the nodule from the adjacent body organs. Thus, if a non-selected image element appears to be a nodule that was not automatically selected by the analysis module 46, the operator can manually select a region of interest (ROI) around the suspected nodule in one or more of the image slices. The analysis module can then perform its analysis of the suspected nodule and provide roundness information, volume information, or the like. Likewise, if a selected nodule appears to be tubular in shape, such data would tell the operator that the nodule is likely part of the patient's vasculature, and not a nodule. If desired, the operator may then de-select the suspected nodule from further tracking for follow up body scans.

Once the nodules are selected for analysis, a grow algorithm in the analysis module 46 can calculate the parameter for each of the selected nodules (Step 56) and the statistics for each of the nodules will be logged as a file into database 14 (Step 58). The algorithm can calculate 3D data for the selected lesion such as volume, major and minor dimensions, density, roundness parameter, gray-level features such as mean and standard deviation, maximum and minimum signal intensity, and the like. The data derived from the image can include histogram statistics for each of the slices separately and for the entire slab/volume of the images. Analysis module 46 of the present invention can allow the user to move between the images slices to allow the operator to determine if the nodule has been properly selected in each of the slices.

In addition to calculating the nodule characteristics, the analysis module 46 can also assign each potential nodule a number or marker. Selecting the marker, typically by clicking on the marker will display the nodule statistics in a panel or chart on the graphical user interface. Such a panel allows the operator to "de-select" a localized nodule if it is determined that the selected element is not a lesion or nodule. The panel displayed on the graphical user interface will typically be only for the slice that is shown in the display 34. In order to view the data for all of the slices, the operator can scroll through all of the slices. If desired, the analysis module can be customizable to display a 3D rendering of the entire volume and the statistics for the entire volume.

If desired, in addition to statistics for lung nodules, the operator can also generate statistics for the lung and other body organs imaged during the scan. For example, it may be desirable to generate statistics for the patient's heart, mediastinum, heart, aorta, chest walls, or the like. The statistics can include data on volume, calcium scoring, surface area, density, or other visual impressions from the operator.

Based on the operator's analysis of the statistics produced by analysis module 46, the operator can enter a diagnosis or recommendation (Step 60). Such information can be entered into the database 14 via user input devices 34 such as a keyboard and mouse. In some embodiments, a report generator module 50 can automatically provide recommendations based on the parameters of the nodules in the images and on patient demographic and medical history information. For example, if a large number of nodules are found, the report generator module 50 can automatically recommend that the patient return in three months for a follow up scan.

If the image dataset is a first scan for the patient, the operator will have the option to create a lung report (Step 62). The report generation module 50 can produce a lung report that shows statistics of the lung images, some lung image cross-sections, recommendations, and the like. A sample lung report is provided in FIGS. 18A to 18D. It should be appreciated that the lung reports of the present invention can take a variety of forms. For example, the lung report can be printed on a printer, sent electronically over the communication network to a patient's physician or patient, displayed electronically on output display, saved on a computer readable medium, or the like.

Figure 6:
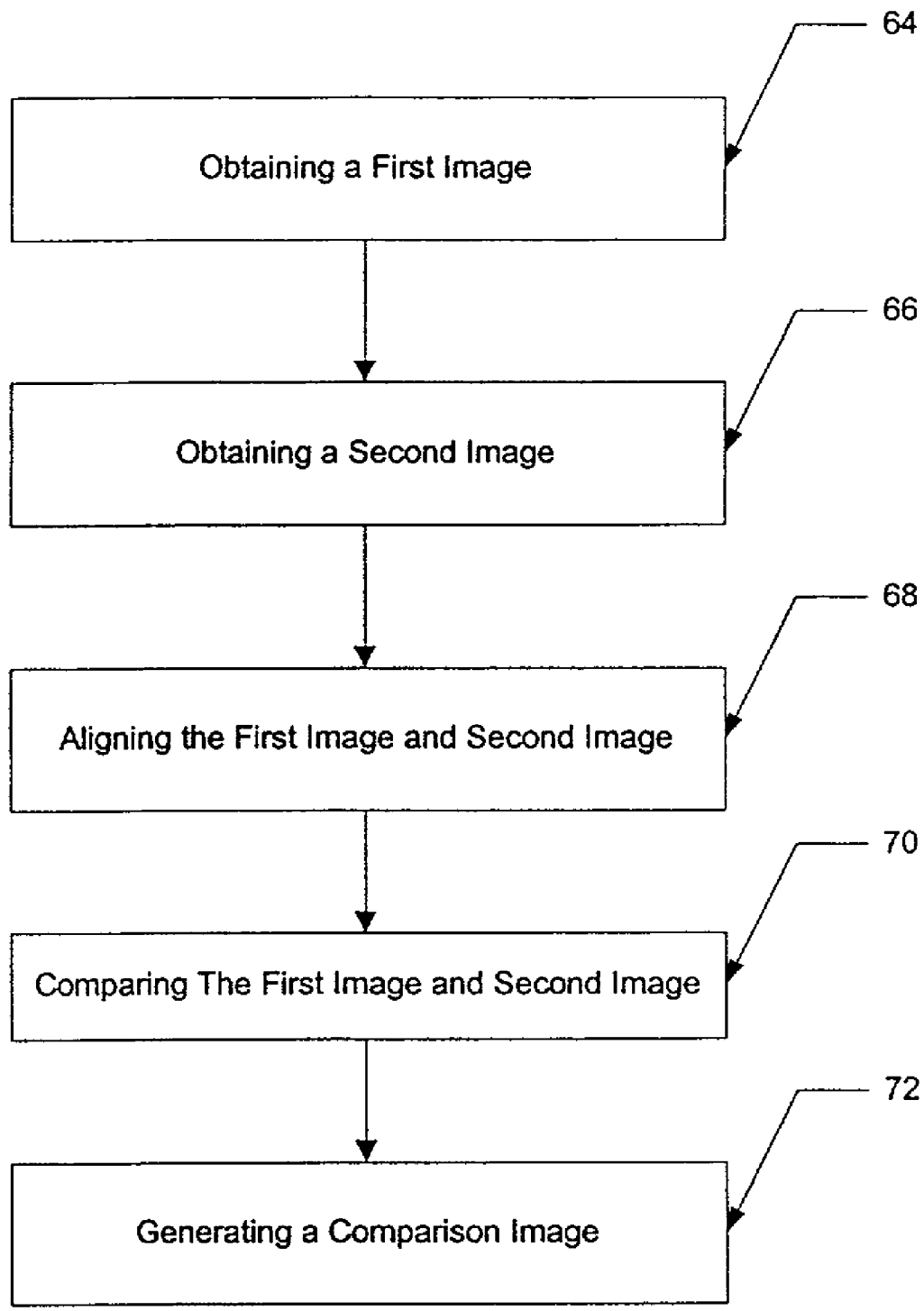
FIG. 6 illustrates a simplified method of generating a comparison image.

If the image dataset is a second, follow-up scan for the patient, the operator will have the option to compare the follow up image dataset with a baseline image dataset of the patient. Using the data logged from the baseline image scan as a starting "map" of the potential nodules in the follow up scan, compare module 48 can automatically relocate the nodules in the follow up images. Automatically localizing the previously assessed nodules in the follow up scan, allows the operator to quickly determine if the previously located nodule(s) are growing or static. FIG. 6 schematically illustrates a simplified method of the present invention for comparing the baseline image dataset with the follow-up image dataset. In general, the first image dataset and second image dataset are acquired at different times and are saved into database 14. (Steps 64, 66). Each of the datasets can then be downloaded into the software of the present invention. Typically, the baseline image can be displayed on the graphical user interface with the corresponding follow up image. An exemplary graphical user interface 100 with comparison functionality is illustrated in FIG. 9. The image(s) from the first and second dataset are substantially aligned or registered along three axis to allow for comparison (Steps 68, 70). Typically, alignment is carried out by making at least one of the images movable to allow the operator to manually move one of the images so as to align the two images with each other. In exemplary methods differences at image acquisition in spatial parameters are automatically corrected using known methods prior to panning the images.

It should be appreciated that in other methods of the present invention, instead of manually aligning the first and second image, the compare module 48 may automatically align the first and second images by matching the major axis of the lung using least square fits or other methodology. It is to be noted that this alignment need not be perfect, since matching criteria can include overlap of any one pixel in each nodule, or even matching by overlap of a "halo" region around each nodule.

If the two images aren't registered, the operator will not be able to properly compare the baseline images with the follow up images. In order to compare the baseline image with the follow up image, the technical imaging parameters of the two images should substantially correspond or be adjusted for such variations. In order to compare the baseline image with the follow up image, the imaging technical parameters (e.g., slice thickness, beam collimation, kV, mAs, Table incrementation, slice overlap, reconstruction parameters) for acquiring the images in the baseline dataset scan and the follow-up image dataset scan should substantially correspond. Nevertheless, methodology exists for correcting for some differences. For instance, images can be rescaled to adjust for spatial resolution, slice thickness, slice overlap and rotation.

One aspect of registering the images is aligning the lung nodules in the two images. One method of matching lung nodules in the two image is implementing software code that requires that at least one voxel in the nodules overlap. Another method of matching nodules is requiring that the edges of the lesions be no more than a fixed number of pixels apart. In exemplary embodiments, the software can require that the edges of the nodules (or other lesion) be no more than one pixel apart, two pixels apart, or three pixels apart. It should be appreciated however, that there are a variety of other methods for registering the images and nodules in the two images.

While changes in imaging parameters such as kV in CT or timing parameters in MRI would impede comparison of tissue characteristics, they would not affect size and volume measurements. It should be appreciated however, that there will inherently be some differences in the baseline and follow-up images due to external factors such as the cardiac cycle or breathing pattern of the patient. Some of these may be ameliorated by retrospective or prospective gating techniques, but, the images will typically not be exactly the same, and matching criteria will be such as to allow some resiliency in the process.

In exemplary embodiments, comparison module 48 illustrates to the operator any changes that may have occurred between the baseline scan and follow up scan. In some embodiments, illustration of the changes in the image datasets includes displaying a comparison image on the user interface display 34 (Step 72). The comparison image will typically be a composite image that can be a subtraction of the first and second image—i.e., all common image characteristics between the first and second image will not be shown and only the differences will be shown. Alternatively, the comparison image can be a sum of the first and second image which shows overlap as brighter than the non-overlapped areas of a nodule. If displayed in color, the baseline scan may mark the nodules in one color (e.g. blue), the follow up scan in another (e.g., yellow) and the overlapped region show in a third color (e.g., green). Alternatively, or in addition to the comparison image, comparison module 48 can provide a statistical chart that shows the changes to the nodules found in the first image dataset. In addition to comparing the nodules in the first and second image dataset, the software of the present invention can also automatically analyze the image datasets to determine if new nodules have formed in the lung tissue since the first image dataset.

After the nodules have been localized and/or compared, the operator can generate a lung report. The lung reports can include data comprising the patient's history, the image data, comparison data to national statistics, radiologist recommendations, prognosis for the number, size and location of nodules found in the scan, or the like. Typically, the software of the present invention can be configured to allow each of the lung reports to be customized. The lung reports can be customizable for each patient, if desired. Alternatively, each of the imaging facilities (or each of the radiologists) can configure the software to produce customized lung reports that are tailored to their needs.

Figure 7:
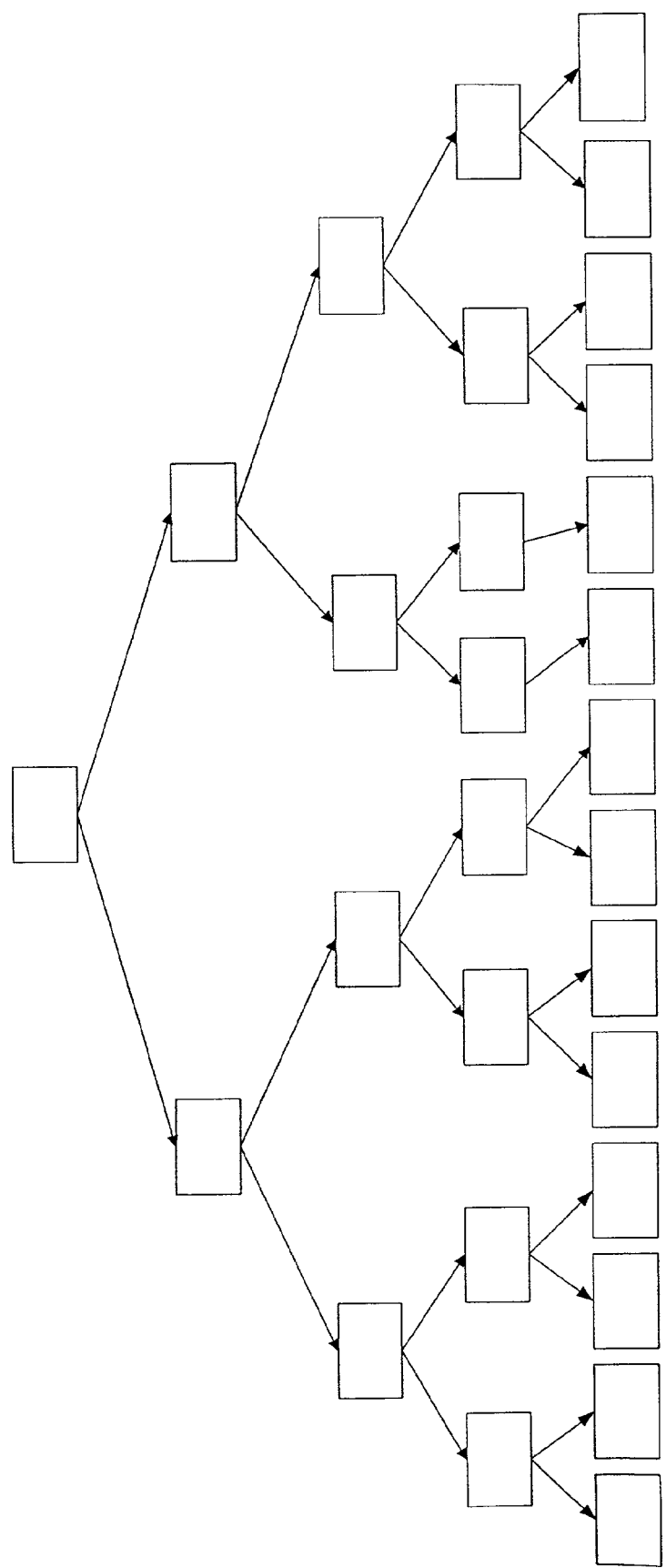
FIG. 7 schematically illustrates a decision tree incorporated into a report generation module of the present invention.

FIG. 7 illustrates a decision tree of the present invention that is incorporated into the report generator module 48. Typically, the report generator module obtains the image analysis data and recommendations that are stored in database 14 regarding the patient's image(s). The report generator module will generate a report that is generated from a programmable decision tree.

Figure 18A:
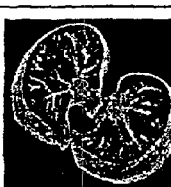

Typically, the operator will be given a choice to choose images for a report. Three dimensional images can be selected prior to generating a report. In addition to displaying the selected images from the scan, if desired, the statistical data can be compared to population data. The other patient data can be derived from database 14 that stores the national percentile data. The patient's position relative to the national percentile can be established with a marker within a chart, as illustrated in FIG. 18C. Criteria for comparison can include smoking history, family history, gender, age, occupational history, and other factors that may be known at the time as influencing the risk factors of a particular individual or his/her prognosis.

There are several aspects to report customization. The first customizable aspect of the body report is the report layout. The layout affects the look and feel of the report. Fields can be laid out in particular locations. To accomplish the report layouts, a list of fields will be created. The list can be tagged with a position marker and the marker can direct the field to a particular place on a page of the report. In this way, the location, number, and order of the field can be chosen by the physician. The library of choices for report elements can be quite large and can include both graphic and text elements. Graphic elements can be fixed (e.g. a histogram of population statistics) or particular to the patient (e.g. an annotated image from the patient set.) Similarly, the text elements can be fixed (e.g. site name and address, or an explanation of the test) or related to the specific results of the study.

Another aspect of the customization is a decision tree or set of logic steps which can connect the fixed information results from the tests (e.g., demographic data) and patient history data. The program code can provide an interface comprising four sections on the computer screen display. In exemplary embodiments, one section can be a list of all the output fields (e.g., recommendations such as "urgent to visit a physician", "need to return in six months", "results are normal for subject's age, gender and medical factors"). The second section can be a list of all the input fields (e.g., subject age, gender, occupational status, number of nodules, size of nodules, and so on). If the lists are longer than can be displayed at one time on the output display, a scroll bar can be used to cycle through the list. The operator can choose by a click an alphabetical or thematic ordering of each list. The third section contains buttons for all needed logic and arithmetic operations (e.g., AND, OR, NOT, GREATER THAN, LESS THAN, EQUAL TO, THEN, NEXT OUTPUT FIELD, FINISH OUTPUT FIELD, SUM, MINUS, DIVIDE, MULTIPLY, etc.) The fourth section contains a graphical representation of the logic tree as it is generated.

In exemplary embodiments, the operator can generate the logic or decision tree without any typing. For example, an output field can first be created by clicking or otherwise selecting the first section. Then, for that output field, a decision tree will be created by clicks on the input fields interspersed with clicks on the logic or arithmetic operators. In essence, the report can be constructed by stringing together various input elements like pearls in a necklace. Editing code can allow the operator to edit the string of fields.

Another customization possibility is the incorporation of information gathered from the aggregation and statistical analysis of previous patient results and outcomes. These previous patients can be those at the client imaging center, as well as those from other imaging centers with which the client center is sharing results data.

Figure 8:
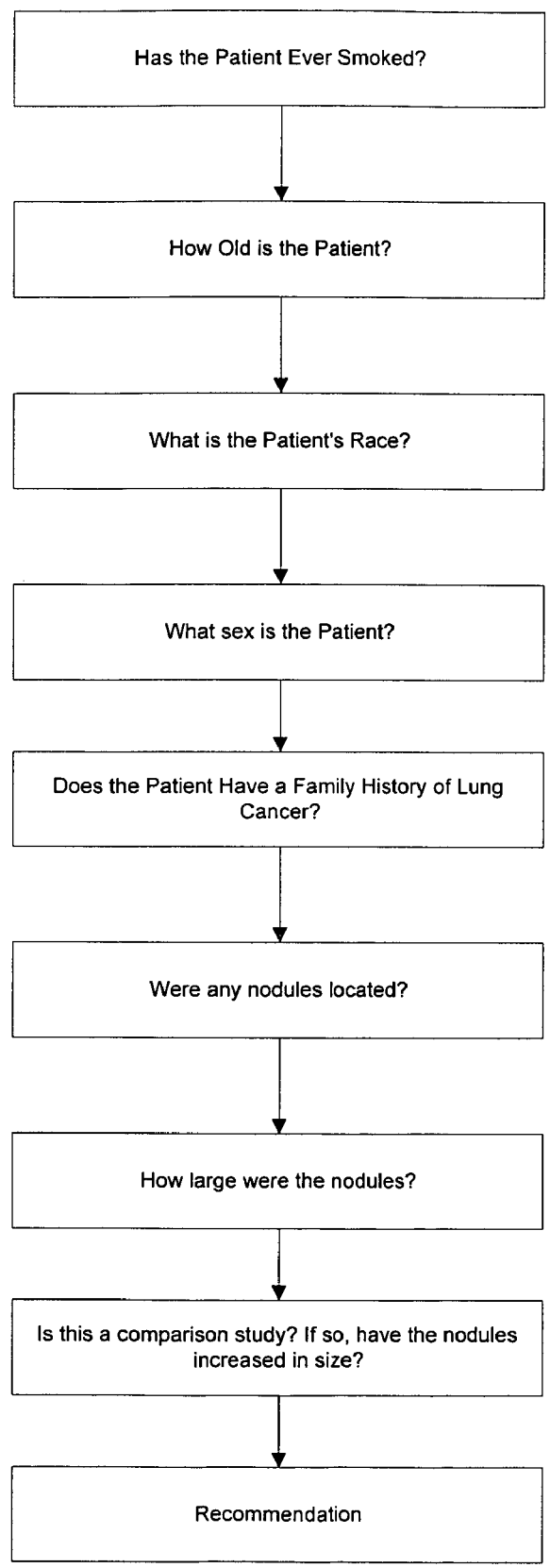
FIG. 8 schematically illustrates an exemplary list of fields in a decision tree of the present invention.

Further customization can occur through incorporation of the decision tree to analyze all of the statistical data collected, so as to give an automated recommendation to the patient. The automated recommendations can be personalized by each radiologist or imaging facility. For example, some radiologists may choose to incorporate data regarding age, race, gender, or the like, while other radiologists may choose to not choose to incorporate such information into his recommendations. FIG. 8 shows sample criteria that may be part of the decision tree:

1. Has the never smoked, moderate smoker, heavy smoker?
2. How old is the patient? below 30, below 50, below 70?
3. Is the patient male or female?
4. What is the patient's race?
5. Does the patient's family have a history of lung cancer?
6. How many nodules does the patient have? less than 5 or more than 5?
7. Are any of the nodules over 1 cm in major axis? 3 cm in axis?
8. Has more than one study been performed? If so, have any of the nodules shown an increase in size?

Based on a combination of such questions or other sets of questions, the report generator module 50 will generate a different recommendation. Some hypothetical examples are as follows:

If the subject:
1. never smoked.
2. age 70.
3. male.
4. has 5 nodules.
5. no nodules over 1 cm in major axis.
6. recommend follow up in 3 years.

If the subject
1. heavy smoker.
2. age 50.
3. male.
4. has 5 modules.
5. one nodule over 3 cm in major axis.
6. recommend urgent follow up with primary physician.

If the subject:
1. never smoked.
2. age 70.
3. male.
4. has 5 nodules.
5. no nodule over 1 cm in major axis.
6. second study shows significant size increase in at least one nodule.
7. recommend urgent follow-up with primary physician.

Typically, the operator will be given the choice to choose between a regular report and a comparison report. If the report generated is a comparison report, the operator must select the first and second datasets that are to be compared. After the dataset is selected, the operator (or decision tree) can choose which information can be incorporated into the lung report. Typically, the information will include statistics for the nodules assessed during analysis, physician data inputs, such as recommendations, or other comments, findings regarding the surrounding organs such as the lungs, mediastinum, heart, thoracic aorta, and chest wall, patient data, such as age, gender, medical history, race, family medical history, smoking history, occupational history, asthma, allergies and other factors that may be known at the time as influencing the risk factors of a particular individual or his/her prognosis, or the like can be incorporated into the report. In some embodiments, the report generator module 48 can use the patient data to tailor any recommendations and conclusions. For example, if a patient has a family history or lung cancer, report generator module 48 can be customized to automatically recommend a follow up scan at a later time, even if no nodules were localized during the first scan.

As shown in FIGS. 9–16, the present invention further provides software code for generating a graphical user interface 100 on a user interface display 34. The graphical user interface 100 can display an image window 102, histograms 104, data graphs or charts 106, and a toolbar 108 for displaying and analyzing the images. For ease of reference, specific names will be used for the various icons and buttons that are present in the graphical user interface toolbar and such names should not be construed to be limiting to the concepts of the present invention One exemplary graphical user interface 100 is illustrated in FIG. 9. In a particular embodiment, toolbar 108 is positioned along a top portion of the display and window 102 is positioned in a lower right portion of the screen. The body image slice illustrated is an axial CT image of the patient's lung. At the bottom of the graphical user interface are icons MPR1, MPR2, and MPR3 icons 110, 112, 114 that allow the user to toggle between different image planes (i.e. axial, coronal, and sagittal).

Graphical user interface toolbar 108 of the present invention will typically have a plurality of buttons or icons that upon activation can manipulate the image displayed in window 102. The icons can include a combination of, but is not limited to, a crossbar button 116, an overlay color button 118, a Draw Region of Interest (ROI) Button 120, a Block selection 122, an Auto Contour Button 124, a Select Lesion 126, an Edit Lesion 128, a 3D button 130, a Frames button 132, Edit Text 134, a Draw Line button 136, a Select Layout button 138, and a Report button 140.

As illustrated in FIG. 9, upon selection of the crossbar button 116, a crossbar 142 will appear on image window 102 that can be positioned by the operator through actuation of a user input device 34 to restrict the area of analysis within window 102. Crossbar 142 can also be used to reference a point in all three planes of the body image. In use, the operator can move a cursor 144 within window 102 and click and hold a button on mouse 34 to drag the crossbar to a desired position in window 102. Upon moving to the desired position, the operator can release the button and the crossbar will be maintained in the desired position. If the operator switches to a multiple plane view (FIG. 10), crossbar 142 can act as a the reference point in the three image planes.

The operator can select the buttons on toolbar 108 to perform various tasks with the image. To begin obtaining data for the nodules in the lung images, the operator can activate the Draw ROI button 120 or the Auto Contour Button 124. Selecting the Draw ROI button 120 will allow the operator to manually draw a region of interest around the potential nodules. If the operator wishes to deselect a ROI, the operator can activate the Block Selection Button 122 to delete the previously selected potential lesion. Activation of Auto Contour Button 124 will activate analysis module 46 so as to automatically draw a ROI around potential nodules that are displayed within the slice displayed in window 102.

After the lesions have been selected in the displayed slice, the operator can repeat the selection process in the remaining slices, until all of the nodules have been selected. It should be appreciated however, that in some embodiments of the software of the present invention, the software may automatically select the nodules in the adjacent image slices or all of the image slices. After the lesions have been selected, the operator may optionally activate the Overlay Color button 118 so that the selected nodules will be displayed in a different color to differentiate the selected nodules from the surrounding tissue. Overlay color button activates analysis module 46 to automatically highlight the selected nodules in the window by changing the colors or intensity of the nodules or other selected tissue. Determination of which color to display the image elements can be based on the grayscale intensity of the selected elements.

In order to display statistics for an individual nodule, the operator can activate the Select Lesion button 126 and move the cursor over the desired nodule. By clicking on the desired nodule, chart 106 will display various statistics of the selected nodule. Some statistics that can be displayed are the anatomic position, number of pixels, area, volume, Value (HU), including minimum, maximum, median, mean, total sum, roundness, standard deviation, diameter 1, and diameter 2.

Figure 10:
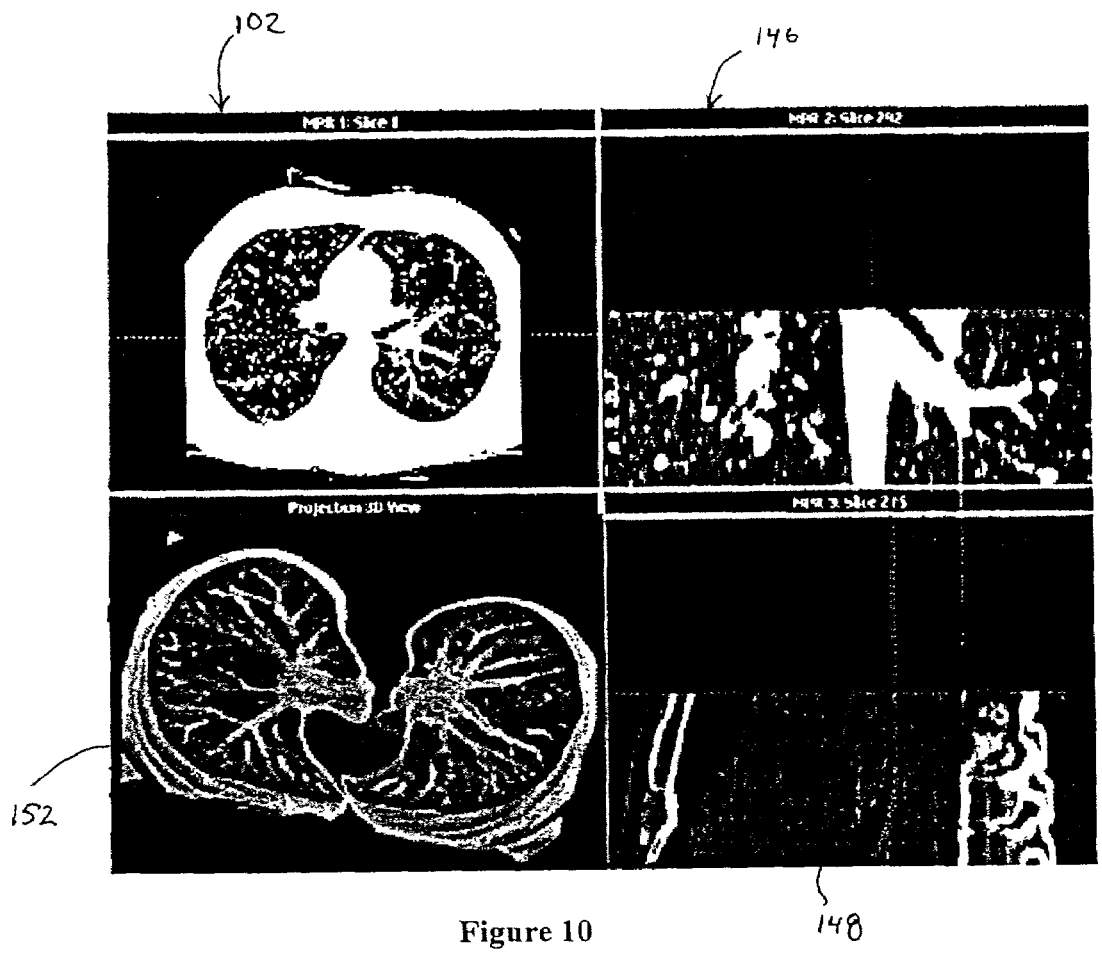
FIG. 10 illustrates an exemplary graphical user interface having a plurality of windows for illustrating different planes of patient's lung.
Figures 11A, 11B, 11C:
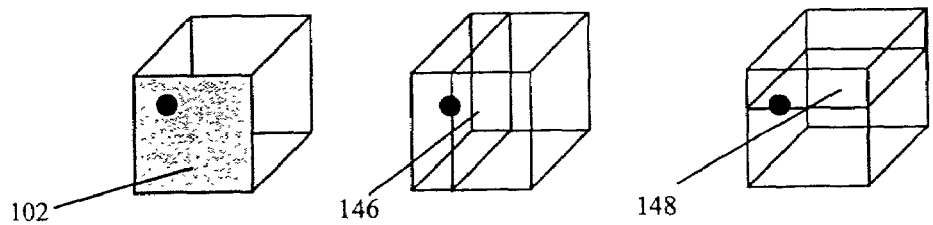
FIGS. 11A to 11C are simplified figures illustrating the axial, sagittal, and coronal image planes.

As shown in FIG. 10, the operator can toggle to a multiple plane view. To change from a single plane view to a multiple plane view, the operator can select the "Select Layout" button 138 on the tool bar 105 to toggle to the three plane view to concurrently display three images along different planes. In this view, three planes of the selected image can be shown simultaneously on the screen as three separate image windows 102, 146, 148. The three viewing planes (e.g., axial 102, sagittal 146, and coronal 148) of the image will be shown and the coronal and sagittal view will have arbitrary locations until the operator chooses, e.g. clicks on a point 150 on one of the three views, the other two views will then display an image that corresponds to the point 150 clicked on by the operator (FIG. 11).

As illustrated in FIG. 10, when all three planes are illustrated, the screen will be split into separate windows, and typically four windows, in which the three image planes can be in the first three windows 102, 146, 148, and a fourth window 152 can contain another image, such as a rendered three dimensional view or an image along an oblique plane. The three dimensional image will 152 provides information as to the relative position of the nodule in the patient's lungs.

While the illustrated embodiment shows the display split up into four separate windows, it may be possible to divide the display into any number of image windows.

To identify the image planes displayed in each window, each of windows 102, 146, 148, 152 can be labeled with a title of the viewing plane, such as "Axial," "Sagittal," and "Coronal."

In an exemplary embodiment, graphical user interface 100 can include a "Frames" button 132 in the toolbar 108 that allows the operator to toggle between concurrent and separate panning and zooming of image windows 102, 124, 126, 128. In a preferred embodiment, the images should start at the same scan FOV and then have concurrent zoom as the default. Activation of Frames button 132, will provide concurrent, proportional zooming and panning between the three image planes. Activating the Frames button 132 a second time will return the software to its default position in which each of windows will have independent zooming and panning in all of windows 102, 146, 148, 152.

If the operator wishes to view only a single pane view, the operator can double click within the selected window that the operator wishes to view. Alternatively, the operator can activate the Select Layout button 138 to toggle between a single plane view and a multiple plane view.

Toolbar 108 can further include a 3D button 140. 3D button toggles between 3D/2D mode for the statistics. When the 3D button is activated, analysis module 46 will display three dimensional statistics for the nodules. For example, in each plane, only partial information on spatial characteristics is available. The 3D button will display the nodule as fully rotatable axes which are controlled by the direction of mouse movement. The user can then see in real time the details of the shape in all axes of the nodule.

Referring now to FIGS. 12–16, the graphical user interface 100 of the present invention can include a variety of tabs or icons 154 that allow the operator to toggle between the various data input/output panels 106 of the graphical user interface. Activating the tabs allows the operator to toggle between the various anatomy tabs input panels. In an exemplary embodiment, the panel 106 includes tabs for the right and left lung, mediastinum, lesions, chest wall and heart and aorta. It should be appreciated, however, that in other configurations of the present invention, graphical user interface 100 can include more or less tabs.

Figure 12:
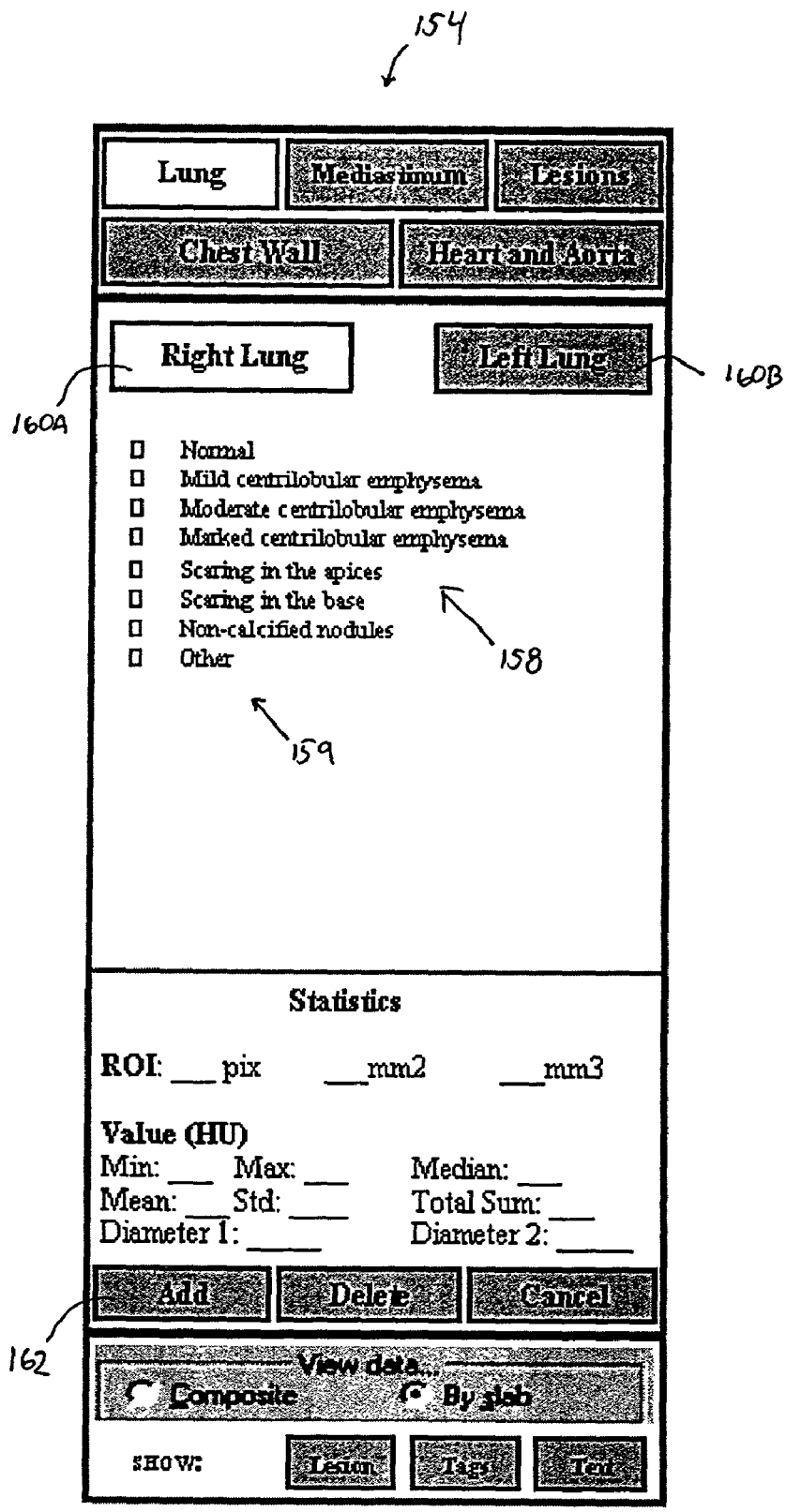
FIG. 12 is an exemplary lung panel of the graphical user interface of the present invention.

FIG. 12 shows Lung Tab Panel 156 of the present invention. The operator can mark his findings from his analysis of the images for both the right and left lung on checklist 158. Clicking on Other 159 will display a text box (not shown) which allows the operator to enter his findings and/or comments that are not found in the main checklist. Typically, the comments entered in the text box, will be displayed in the lung report that is generated by report generator module 50. To toggle between the left and right lung, operator can click on or otherwise activate the left or right lung tab 160a, 160b. Clicking on add button 162 will store the operator's findings in database 14. Optionally, the stored data can be compared with national percentile data, and the report generator module 50 can produce recommendations based on where the patient's data is relative to the national percentile data.

FIG. 13 shows a mediastinum panel 164 of the present invention. The mediastinum panel 164 has a similar checklist 166 that allows the operator to input his findings.

FIG. 14 shows a Heart and Aorta tab 168. In this tab, the operator can enter his visual impression on the heart size and the condition of the aorta. In some configurations, the analysis module 46 will be programmed to calculate the volume of the heart, measure the long and short axes, provide calcium scoring of the coronary vessels and aorta, and the like.

FIG. 15 shows a chest wall and spine tab 170 that allows the operator to enter his findings and recommendations about the chest wall and spine.

FIG. 16 shows a lesion/nodule tab 172. When a lesion is selected, either automatically by the analysis module 48 or manually by positioning a ROI around the potential nodule, analysis module 48 analyzes the nodule selected and calculates all of the statistics (e.g., volume, surface area, roundness, density, HU values, and the like). Analysis module 48 can also filter out surrounding vessels around the nodule, if desired by the operator.

In some embodiments, the operator can click on the lesions to add it to list 174. In other configurations, analysis module 48 can automatically add the selected lesions to list 174. The operator can revise the list of lesions by clicking on the potential lesion to select the lesion and click on the delete button 176 or edit button 128 on toolbar 108. The lesion list 174 will characterize the lesions by its number, location, pixel size, surface area, volume, two diameters (longest and shortest), mean value, min/max, and median. The list of all of the tagged nodules provides the operator with the ability to review and edit the selected nodules, based on his observation of the statistics. A total list 178 can be used to show the total statistics for all of the tagged lesions.

Figure 17:
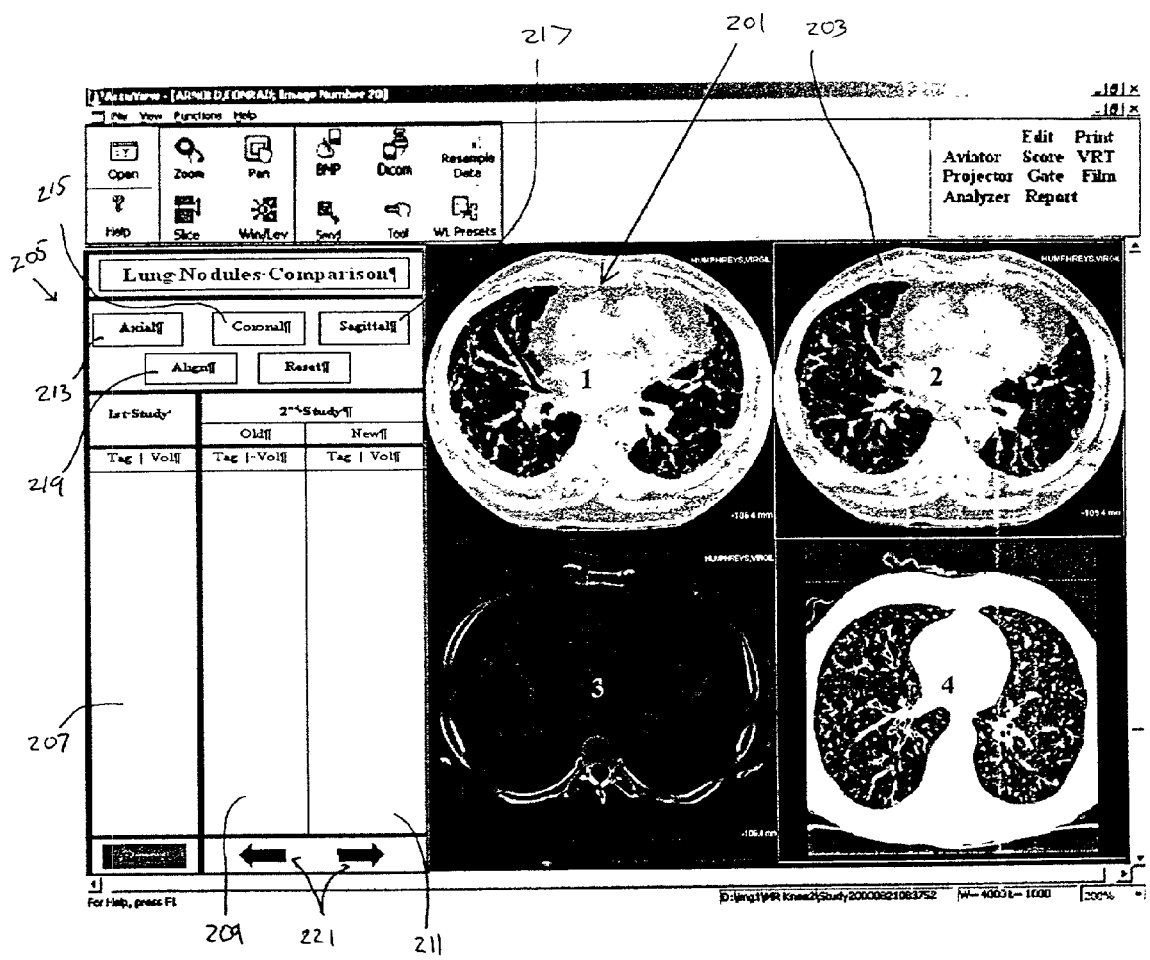
FIG. 17 is an exemplary graphical user interface for comparing a baseline image with a follow-up image.

If the operator chooses to compare two image dataset, the operator must select the two studies for comparison from database 14. Once the operator has selected the two studies, the software of the present invention will generate graphical user interface 200, as shown in FIG. 17. After the two studies are chosen, graphical user interface 200 will display at least two windows 201, 203 for displaying images from the first and second study. In exemplary embodiments, graphical user interface will include a lung nodule comparison panel 205 for displaying the statistics for the nodules in the first and second studies. As shown, the panel will include a portion for displaying the tagged nodules and their statistics for the first study 207, a portion for displaying the old tagged nodules and their statistics 209, and a portion for displaying any newly located nodules 211.

Lung nodule comparison panel 205 can include an axial button 213, coronal button 215, and sagittal button 217 for displaying corresponding images of the first and second study in their respective image planes in windows 201, 203.

After the first and second studies have been opened, the operator can align the first and second studies in all three planes. Alignment can be carried out manually by panning at least one of the images until the first and second images are aligned. Alternatively, the comparison module 48 can be activated, typically via an input button on the graphical user interface, to automatically align the first and second images.

In exemplary embodiments, activating the align button 219 starts a calculation process in the comparison module 48 to list all of the known nodules in the first study and to determine if any of the nodules localized in the second study are new or old. Criteria for determining whether a localized nodule in the second study is new or old can take a variety of forms. One example, one method of determining of a nodules is new or old is to determine there are N amount of common pixels of the nodules found in the first study and a nodule in the second study.

After the calculating process has been completed, the comparison data is posted into portions 207, 209, 211, respectively. If the nodule was incorrectly placed in the wrong portion of panel 205, the operator can choose the nodule and click on arrows 221 to move the chosen nodule to the correct portion. The comparison data can thereafter be saved as a separate file in database 14.

Once the operator has reviewed and tagged all of the nodules, and in the case of comparison studies analyzed the old nodules and located all of the new nodules, the operator can activate the Report button 180 to generate the lung report for the patient. An exemplary lung report 200 is illustrated in FIGS. 18A–18D. It should be appreciated that the lung report 200 illustrated is merely a sample lung report, and that the lung report of the present invention is customizable by the operator to display customizable data and recommendations.

The lung reports of the present invention will vary depending on whether the image dataset is a first study for the patient or a comparison study between a baseline and follow-up study. As illustrated in FIG. 18A, the lung report will typically list the patient information 202 that is stored in database 14. The lung report can also list the parameters of the imaging procedure 204. Since each of the lung report is customizable, depending on what the operator (or imaging facility) has entered into the fields of the decision tree (FIGS. 7 and 8), each of the lung reports will typically have different recommendations, and some lung reports may not list the patient information or information regarding the imaging procedure.

Figure 18B:
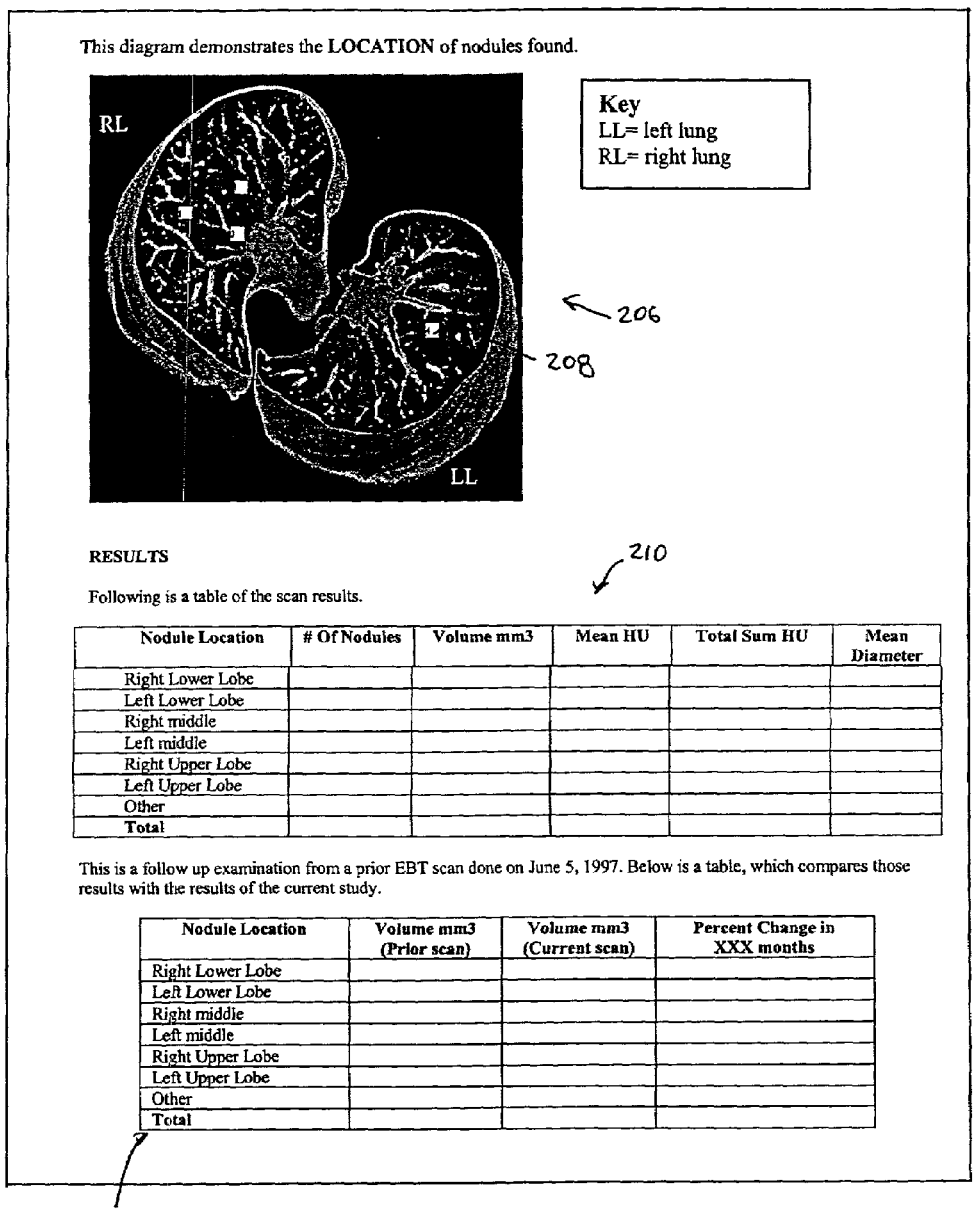
Figure 18C:
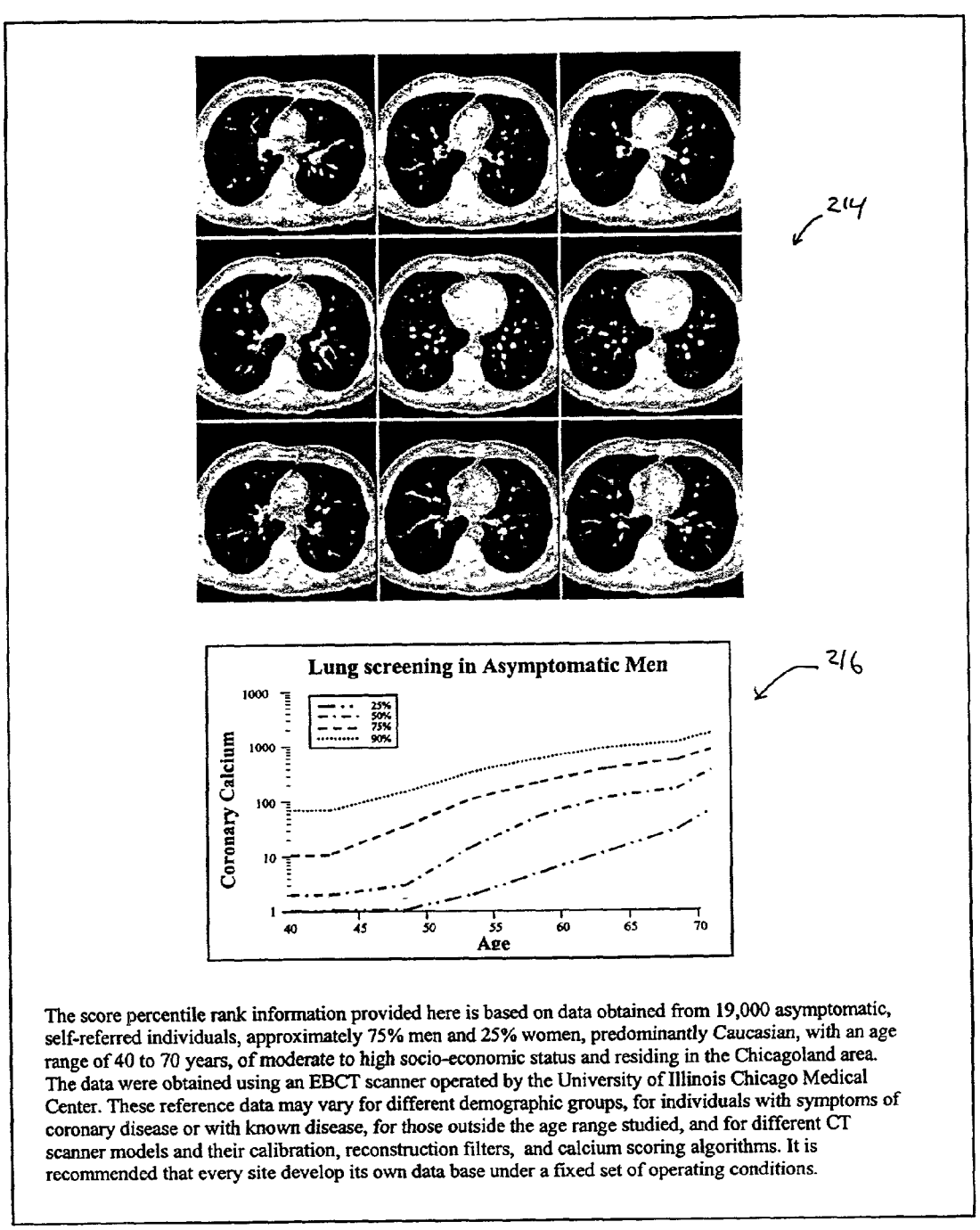

As shown in FIG. 18B, typically the lung report 200 will include a mapped image 206 illustrating the location of the nodules. As illustrated, the locations of the nodules are shown by numbered markers 208. A nodule chart 210 can be used to provide data as to the position of the nodules, the number of nodules in each area of the lung, the volume of the nodule, the area of the nodule, mean diameter, mean HU, Total Sum HU, roundness or surface regularity parameters, or other parameters of the nodule.

In cases where the lung report is a follow up study, the lung report 200 can include a comparison chart 212 which lists the nodules statistics from the baseline study—typically in the form of volume, the number of nodules etc. The statistics from the baseline study can then be compared with the statistics from the follow up scan so as to display new nodules and any percentage change in size of the old nodules.

As illustrated in FIG. 18C, lung report 200 can further include selected body lung images, from the baseline study and/or the follow up study to display various slices of the lungs 214. Optionally, lung report 200 can also include a score percentile rank information 216 to show the patient where he or she ranks in relation to other patients of similar backgrounds.

FIG. 18D illustrates lung report 200 that includes the operator's findings 218 from his analysis of the lung slice image dataset. Typically, the findings are derived from the operator's inputs into the graphical user interface input panels (FIGS. 12–16). Conclusions 220 will generally provide customizable recommendations. The recommendations will typically be produced through the various factors listed above.

In another aspect, the present invention provides a database 14 of lung nodule statistics (FIG. 1). Information from the database can be used to guide the software decision tree to customize the lung report and to guide a treatment recommendation.

In exemplary databases 14 of the present invention, the database can be accessed over a communication network, like the internet, and can be used to store lung information of the population. The population lung information can be used to determine an individual patient's standing relative to other people of a similar demographic so as to provide a customized recommendation based on the patient's percentile ranking.

In exemplary embodiments, database 14 can store population information in the database for every person scanned regarding each nodule. Such information can include, but is not limited to, nodule information such as the location of the nodule with respect to anatomic landmarks, volume of the nodule, major and minor axis of the nodule, an index of the nodule's roundness, surface area, average signal intensity, standard deviation, maximum and minimum pixel intensity and patient information, such as age, race, gender, smoking history, demographics, geographic location, diet, or the like.

In addition to the above nodule information, the database of the present invention can further store the number of nodules, total nodule mass, and demographics of each of the particular patients. From this database, one can build an expectation value for people in the population with similar demographics (e.g., age, gender, race, smoking pattern, diet, geographic location, and the like).

The population lung information can be searched and sorted using known methods. Typically, the database can be searchable based on at least one of the nodule statistics and/or patient fields. As the database is developed, it will be possible to allow imaging facilities from around the world to access the database and to compare the individual patient's lung nodule information with the population data of people of similar demographics. Typically, the information from each of the individual data scans can also be logged into the database so as to update the database and allow radiologists from around the country to compare the outcome of the patient's case study with other similar case studies.

When survival rates for different populations and nodule burdens become known through development of the database, the same database can be used to provide the lung information based on demographics and nodule burden. As can be understood, as this information is accumulated there will be additional information generated, for instance, whether the location of the nodules in the lung, or their proximity, may change risk factors and recommendations.

As can be appreciated, the stored information in the database can be used to guide the decision tree of the present invention regarding the customization of the lung report generator. It is understood that the risk and recommendations are dynamic and may change in response to the information accumulated in the database, or elsewhere. For example, a male of 50 years of age, with a history of smoking having a burden of five nodules under 3 mm maximum dimension which would be in a high risk group if the database information shows that the norm for this age and smoking history is 1 nodule not to exceed 5 mm.

After the patient lung information has been compared, the software of the present invention can provide a customized recommendation in the lung report 300 indicating the recommendations of the physician based on any combination of the patient's age, race, gender, smoking history, demographics, nodule information, and the like. Additionally, the lung report can provide a graph or chart that illustrates where the patient is relative to national rankings. (FIG. 18C).

While the above is a complete description of the preferred embodiments of the inventions, various alternatives, modifications, and equivalents may be used. For example, while the above methods recite methods of comparing lesions in a first image with the corresponding lesions in a second image, it should be appreciated that the present invention can be used to compare a "clean" baseline image with a second, follow up image to determine if any lesions have formed since the baseline image scan was taken. Although the foregoing has been described in detail for purposes of clarity of understanding, it will be obvious that certain modifications may be practiced within the scope of the appended claim.

What is claimed is:

1. A system for displaying a graphical user interface for analyzing quantitative changes in physical parameters of lung nodules over time, the system comprising:
   a processor;
   a memory configured to store at least one first body image taken at a first known time point ($t_1$) and at least one second body image taken at a second known time point ($t_2$), at least one of the first body images and at least one of the second body images being taken from at least one three-dimensional image set along substantially a common plane; and
   a display configured to output the graphical user interface, the graphical user interface comprising:
      the first body image corresponding to the common plane taken at $t_1$;
      the second body image corresponding to the common plane taken at $t_2$;
      a region for displaying quantitative information for one or more lung nodules imaged at $t_1$ along the common plane and determined using the at least one first body image and quantitative information for one or more corresponding lung nodules imaged at $t_2$ along the common plane and determined using the at least one second body image, the quantitative information comprising information related to at least one three-dimensional parameter associated with the one or more corresponding lung nodular; and
      a region for displaying quantitative changes in at least one of the corresponding lung modules between the first and second time points, the quantitative changes including a rate of change in at least one three-dimensional parameter in at least one of the corresponding lung nodules between the first and second known time points computed automatically based on the first and second body images.

2. The system of claim 1 wherein the graphical user interface further comprises an electronic map representing the position of at least one nodule in the first body image and position of a corresponding nodule in the second body image.

3. The system of claim 2 wherein the electronic map comprises at least one marker.

4. The system of claim 3 wherein the marker is a number, a symbol, or a color.

5. The system of claim 1 wherein the composite image comprises an electronic representation of a subtraction of the first body image and the second body image.

6. The system of claim 1, the graphical user interface further comprising an electronic three dimensional representation of the first or second image.

7. The system of claim 1, the graphical user interface further comprising a toolbar for manipulating at least one of the first image and second image.

8. The system of claim 1 wherein the parameter comprises at least one of size, cross-sectional area, volume, surface area, roundness, density and standard deviation, and major and minor axes of a nodule.

9. The system of claim 1 wherein the comparison panel comprises a first portion for displaying quantitative information for nodules in the first image and a second portion for displaying quantitative information for the corresponding nodules in the second image.

10. The system of claim 9, the graphical user interface further comprising a third portion for displaying statistics of new nodules in the second image.

11. The system of claim 1 wherein the graphical user interface further comprises means for enabling the user to establish a correspondence between the first nodule in the first body image and another nodule in the second body image.

12. The system of claim 1, the graphical user interface comprising a report input button for generating a lung report.

13. The system of claim 1 wherein the correspondence between the first nodule in the first body image and the first nodule in the second body image is automatically determined by a program executed by a processor.

14. The system of claim 1 wherein the parameter is user-selectable.

15. The system of claim 1 further comprising an option enabling a user to dissociate the first nodule in the first body image from the first nodule in the second body image such that the first nodule in the second body image is no longer identified as corresponding to the first nodule in the first body image, whereby the display of quantitative changes is updated in response to the dissociation.

16. The system of claim 1 further comprising an option enabling a user to associate unassociated nodules in the first and second body images, whereby the display of quantitative changes is updated in response to the association.

17. The system of claim 1 wherein the rate of change is recalculated automatically upon changes in association of lung nodules in the first and second body images.

18. A system for analyzing quantitative changes in physical parameters of lesions over time, the system comprising:
   a storage device for storing a first three-dimensional dataset of images captured at a first known time point and a second three-dimensional dataset of images captured at a second known time point, at least one of the images in each of the first and second datasets being taken along a substantially common plane;
   an output device; and
   a processor coupled to the storage device and the output device, the processor programmed to:
      cause the output device to output an image from the first dataset and an image from the second dataset;
      compare a lesion in the image from the first dataset and a lesion in the image from the second dataset that is determined by software code executed by a processor to match the lesion in the image from the first dataset;
      cause the output device to display, based upon the comparison, one or more quantitative changes in the lesion between the first and second known time points, the quantitative changes including a rate of change in at least one three-dimensional parameter of the lesion between the first and second known time points; and
      cause the output device to output an option that enables a user to indicate that the lesion in the image from the first dataset matches another lesion in the image from the second dataset instead of the lesion in the image from the second dataset determined by the software code to march the lesion in the image from the first dataset; and compare the lesion in the image based upon the first dataset and the another lesion in the image from the second dataset.

19. The system of claim 18 wherein the processor is further programmed to produce a report.

20. The system of claim 19 wherein the processor is further programmed to electronically deliver the report over a communication network to a third party.

21. The system of claim 19 wherein the processor is further programmed to save the report on a computer readable medium.

22. The system of claim 19 further comprising a printer to print the report.

23. The system of claim 18 wherein the lesions comprise lung nodules.

24. The system of claim 18 wherein the first dataset is a baseline image scan taken at a known time $t_1$ and the second dataset is a follow-up image scan taken at a known time $t_2$.

25. The system of claim 18 wherein the processor is programmed to register the image from the first dataset and the image from the second dataset prior to comparing he lesions.

26. The system of claim 18 further comprising an imaging device for generating at least one of the first dataset or second dataset of images.

27. The system of claim 18 wherein the processor is programmed to compare a parameter value associated with the lesion in the image from the first dataset with a parameter value associated with the matching lesion in the image from the second dataset, wherein the parameter is at least one of cross-sectional area, volume, surface area, roundness, density and standard deviation, major and minor axes of the lesions.

28. The system of claim 18 wherein the processor displays the one or more differences by displaying an image generated by superimposing the image from the first dataset with the image from the second dataset.

29. A system for displaying body images on an output device, the system comprising:
means for displaying a first image of a first three-dimensional image set captured at a first known time point in a first image window;
means for displaying a second image of a second three-dimensional image set captured at a second known time point in a second image window;
means for displaying a third image in a third window, wherein the third image is one of a sum or a subtraction of the first and second image; and
means for displaying quantitative information for at least one lesion related to at least one three-dimensional parameter associated with the at least one lesion in the first and second images;
means for displaying a rate of change in the at least one three-dimensional parameter between the first and second time points; and
means for enabling a user to specify that a lesion in the first image corresponds to another lesion in the second image instead of the lesion in the second image previously determined to correspond to the lesion in the first image.

30. The system of claim 29 further comprising a toolbar displaying user actuatable icons.

31. The system of claim 29 further comprising means for creating a panel for displaying image information of the first image.

32. The system of claim 18 wherein the processor is configured to:

cause the output device to output a panel that comprises information related to a parameter of the lesion in the image from the first dataset and information related to the parameter of the matching lesion in the image from the second dataset; and
cause the output device to output quantitative information indicating a change in the parameter for the lesion in the image from second dataset when compared to the matching lesion in the image from the second dataset.

33. A method in a computer system for analyzing quantitative changes in physical parameters of lesions over time, the method comprising:
receiving a first body image of a first three-dimensional image set obtained at a first known time point, the first body image comprising one or more lesions;
receiving a second body image of a second three-dimensional image set obtained at a second known time point, the second body image comprising one or more lesions;
displaying quantitative information for at least one corresponding lesion in the first and second body images,
displaying rate of change information between the first and second known time points for at least ore three-dimensional parameter of at least one corresponding lesion determined based upon a comparison of the quantitative information;
enabling a user to change the correspondence between the at least one lesion in the first and second body images;
receiving a signal indicating that the correspondence has been changed; and
updating the change information responsive to receiving the signal.

34. The method of claim 33 wherein:
enabling the user to change the correspondence comprises enabling the user to indicate that at least one lesion in the first body image does not correspond to at least one lesion in the second body image; and
receiving the signal comprises receiving a signal indicating that the at least one lesion in the first body image does not correspond to at least one lesion in the second body image.

35. The method of claim 33 wherein:
enabling the user to change the correspondence comprises enabling the user to indicate that another lesion in the second body image corresponds to the at least one lesion in the first body image instead of the first lesion;
receiving the signal comprises receiving a signal indicating that the at least one lesion in the first body image corresponds to the another lesion in the second body image; and
updating the change information comprises displaying updated change information determined based upon a comparison of the quantitative information for the at least one lesion in the first body image and the corresponding another lesion in the second body image.

36. The method of claim 33 wherein the parameter is selectable by the user from a plurality of parameters.

37. The method of claim 36 wherein the plurality of parameters comprises one or more of size, cross-sectional area, volume, surface area, roundness, density and standard deviation, and major and minor axes of the lesions.

38. The method of claim 33 wherein the correspondence between the at least one lesion in the first body image and at least one lesion in the second body image is automatically determined by a program executed by a processor.

39. The method of claim 33 wherein the one or more lesions in the first body image and the second body image comprise one or more lung nodules.

40. The method of claim 33 wherein:
  enabling the user to change the correspondence comprises enabling the user to indicate that the another lesion in the second body image does not correspond to any lesion in the first body image; and
  receiving the signal comprises receiving a signal indicating that the another lesion in the second body image does not correspond to any lesion in the first body image.

41. A system for analyzing quantitative changes in three-dimensional parameters of nodules over time, the system comprising:
  a storage device for storing a first three-dimensional dataset of images captured a a first known time point $t_1$ and a second three-dimensional dataset of images captured at a second known time point $t_2$, at least one of the images in each of the first and second datasets being taken along a substantially common plane;
  an output device; and
  a processor coupled to the storage device and the output device, the processor programmed to:
   (a) automatically make a match for a first nodule in the first three-dimensional dataset captured at first known time point $t_1$ and a second nodule in the second three-dimensional dataset captured at second known time point $t_2$;
   (b) automatically consider the first nodule captured at first known time point $t_1$ to be resolved;
   (c) automatically consider the second nodule captured at second known time point $t_2$ to be new;
   (d) automatically determine a rate of change of an operator-selectable three dimensional parameter for the matched first and second nodules between the first and second known time points;
   (e) provide an operator with the opportunity to inspect the match and the ability to dissociate the matched first and second nodules;
   (f) provide an operator with the ability to associate nodules in the first and second three-dimensional datasets to generate new matches; and
   (g) automatically repeat steps (b)–(d) each time an operator dissociates a match or associates a new match.

* * * * *